United States Patent [19]

Dorsch et al.

[11] Patent Number: 5,389,292
[45] Date of Patent: * Feb. 14, 1995

[54] DIFLUOROMETHYL COMPOUNDS

[75] Inventors: Dieter Dorsch, Darmstadt; Ekkehard Bartmann, Erzhausen; Hans A. Kurmeier, Seeheim-Jugenheim; Ulrich Finkenzeller, Plankstadt; Georg Weber, Erzhausen; Herbert Plach, Darmstadt; Eike Poetsch, Mühltal, all of Germany

[73] Assignee: Merck Patent Gesellschaft Mit Beschrankter Haftung, Darmstadt, Germany

[*] Notice: The portion of the term of this patent subsequent to Jun. 16, 2009 has been disclaimed.

[21] Appl. No.: 845,818

[22] Filed: Mar. 9, 1992

Related U.S. Application Data

[63] Continuation of Ser. No. 424,219, filed as PCT/EP89/00821, Jul. 26, 1989, abandoned.

[30] Foreign Application Priority Data

Jul. 27, 1988 [DE] Germany ............................ 3825425
Mar. 24, 1989 [DE] Germany ............................ 3909802

[51] Int. Cl.$^6$ ...................... C09K 19/34; C09K 19/30; C09K 19/12; C09K 19/20
[52] U.S. Cl. .............. 252/299.61; 252/299.6; 252/299.63; 252/299.64; 252/299.65; 252/299.66; 252/299.67
[58] Field of Search ........... 252/299.01, 299.6, 299.61, 252/299.63, 299.64, 299.65, 299.66, 299.67

[56] References Cited

U.S. PATENT DOCUMENTS

| | | | |
|---|---|---|---|
| 3,506,718 | 4/1970 | Mutsch | 260/609 |
| 3,998,972 | 12/1976 | Farooq et al. | 424/337 |
| 4,048,235 | 9/1977 | Karrer | 360/612 R |
| 4,393,231 | 7/1983 | Misaki et al. | 252/299.01 |
| 4,512,636 | 4/1985 | Andrews et al. | 252/299.01 |
| 4,630,897 | 12/1986 | Andrews et al. | 252/299.01 |
| 4,678,811 | 7/1987 | Franke et al. | 514/721 |
| 4,726,911 | 2/1988 | Krause et al. | 252/299.61 |
| 4,871,470 | 10/1989 | Wachtler et al. | 252/299.61 |
| 4,874,545 | 12/1989 | Heppke et al. | 252/299.01 |
| 4,877,548 | 10/1989 | Kitano et al. | 252/299.63 |
| 4,880,562 | 11/1989 | Kitano et al. | 252/299.63 |
| 4,886,619 | 12/1989 | Janulis | 252/299.01 |
| 4,886,620 | 12/1989 | Hopf et al. | 252/299.61 |
| 5,032,313 | 7/1991 | Goto et al. | 252/299.01 |
| 5,045,229 | 9/1991 | Bartmann et al. | 252/299.63 |
| 5,082,587 | 1/1992 | Janulis | 252/299.61 |
| 5,122,295 | 6/1992 | Weber et al. | 252/299.63 |

FOREIGN PATENT DOCUMENTS

| | | |
|---|---|---|
| 0193191 | 9/1986 | European Pat. Off. . |
| 0387032 | 9/1990 | European Pat. Off. . |
| 3511111 | 10/1986 | Germany . |
| 3906040 | 9/1989 | Germany . |
| 55-157523 | 12/1980 | Japan . |
| 58-18326 | 2/1983 | Japan . |
| 2162515 | 2/1956 | United Kingdom . |
| 88/08441 | 11/1988 | WIPO . |

OTHER PUBLICATIONS

Titov et al., Molecular Crystals Liquid Crystals, vol. 47, (1978), pp. 1–5.

*Primary Examiner*—Philip Tucker
*Attorney, Agent, or Firm*—Millen, White, Zelano, & Branigan

[57] ABSTRACT

Compounds of the formula I $$R-(A^1-A^1)_m-A^2-Q-CHF_2 \quad \quad I$$

in which R, $A^1$, $Z^1$, m, $A^2$ and Q have the meaning given in Patent Claim 1 are suitable as components of liquid-crystalline media.

16 Claims, No Drawings

DIFLUOROMETHYL COMPOUNDS

This application is a continuation of application Ser. No. 07/424,219, filed as PCT/EP89/00821, Jul. 26, 1989, now abandoned.

The invention relates to difluoromethyl compounds of the formula I

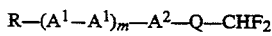

in which
R is H, halogen, —CN, —NCS, an unsubstituted, CN— or CF$_3$-monosubstituted or at least halogen-monosubstituted alkyl or alkenyl radical having 1 to 15 carbon atoms, in which one or more CH$_1$ groups in these radicals, independently of one another, can each also be replaced by —O—, —S—,

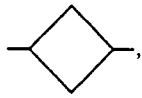

—CO—, —CO—O—, O—CO— or —O—CO—O— in such a manner that oxygen atoms are not directly linked to one another, A$^1$ and A$^2$, independently of one another, is (sic) each a
(a) trans-1,4-cyclohexylene radical in which one or more non-adjacent CH$_2$ groups can also be replaced by —O— and/or —S—,
(b) 1,4-phenylene radical in which one or two CH groups can also be replaced by N,
(c) radical from the group consisting of 1,4-cyclohexenylene, 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
in which the radicals (a) and (b) can be substituted by CN or fluorine, Z$^1$ independently of one another is (sic) are each —CO—O—, O—CO—, —CH$_2$O—, —OCH$_2$—, —CH$_2$CH$_2$—, —CH=CH—, —C—C— or a single bond, m is 1, 2 or 3 and
Q is alkylene having 2 to 6 carbon atom/s in which a CH$_2$ group can also be replaced by —O—, —S—, —CO—O— or —O—CO—, —O—, —S—, —CH$_2$—, —CO—O—, —O—CO— or a single bond,
with the proviso that Q is alkylene having 2 to 6 carbon atoms in which one CH$_2$ group can also be replaced by —O—, —S—, —CO—O— or —O—CO—, —S—, —CH$_2$—, —CO—O—, —O—CO— or a single bond, provided R—(A$^1$—Z$^1$)$_m$-A$^2$— is

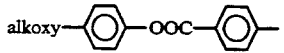

or

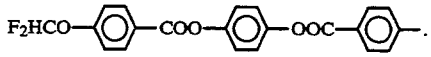

The invention furthermore relates to the use of these compounds as components of liquid-crystalline media and liquid crystal and electrooptical display elements containing the liquid-crystalline media according to the invention.

The compounds of the formula I can be used as components of liquid-crystalline media, in particular for displays based on the principle of the twisted cell, the guest-host effect, the effect of the deformation of aligned phases or the effect of dynamic scattering.

The object of the invention was to find new stable liquid-crystalline or mesogenic compounds which are suitable as components of liquid-crystalline media and in particular simultaneously have a comparably low viscosity and a relatively high dielectric anisotropy.

It has now been found that compounds of the formula I are highly suitable as components of liquid-crystalline media. In particular, they have comparably low viscosities. With their aid, it is possible to obtain stable liquid-crystalline media having a broad mesophase range and advantageous values for optical and dielectric anisotropy.

Compounds which have liquid-crystalline properties and a terminally bound OCHF$_2$ group are already known. On the one hand, crystal structure investigations have been carried out with Schiff bases [S. V. Sereda et al. in Kristallografiya, 32 (5), 1165 (1987) and ibid. 33 (1) 118 (1988)]. On the other hand, V. V. Titov et al. have described in Mol. Cryst. Liq. Cryst. 47 (1–2), 1 (1978) benzoic esters which carry an OCHF$_2$ group in the para position. However, the known compounds are unstable or unusable in commercial displays.

By providing the compounds of the formula I, very generally the range of liquid-crystalline substances which are suitable under various aspects relating to their application for the preparation of liquid-crystalline mixtures is furthermore considerably widened.

The compounds of the formula I have a wide application range. Depending on the selection of the substituents, these compounds can serve as basis materials of which liquid-crystalline media are predominantly composed; however, it is also possible to add liquid-crystalline basis materials from other classes of compounds to the compounds of the formula I, in-order to effect, for example, dielectric and/or optical anisotropy of such a dielectric and/or to optimize its threshold voltage and-/or its viscosity.

The compounds of the formula I are colourless in their pure state and form liquid-crystalline mesophases in a temperature range favourable for electrooptical use. They are chemically and thermally stable and resistant to light.

The invention accordingly relates to the compounds of the formula I and the use of these compounds as components of liquid-crystalline media. The invention further relates to liquid-crystalline media containing at least one compound of the formula I and to liquid crystal display elements, in particular electrooptical display elements containing this type of media.

For the sake of simplicity, in what follows X is Q-CHF$_2$, Cyc a 1,4-cyclohexylene radical, Che a 1,4-cyclohexenylene radical, Dio a 1,3-dioxane-2,5-diyl radical, Dit a 1,3-dithiane-2,5-diyl radical, Phe a 1,4-phenylene radical, Pyd a pyridine-2,5-diyl radical, Pyr a pyrimidine-2,5-diyl radical, Pip a piperidine-1,4-diyl radical, Nap a naphthalene-2,6-diyl radical, Dec and Tet a decahydronaphthalene radical and a 1,2,3,4-tetrahydronaphthalene radical and Bi a bicyclo[2.2.2]octylene radical in which Cyc and/or Phe can be unsubstituted or monosubstituted or disubstituted by F or CN.

The compounds of the formula I accordingly comprise compounds having two rings of the partial formulae Ia and Ib:

R-A$^1$-A$^2$-X  Ia

R-A$^1$-Z$^1$-A$^2$-X  Ib

Compounds having three rings of the partial formulae Ic to If:

R-A$^1$-A$^1$-A$^2$-X  Ic

R-A$^1$-Z1-A1-Z1-A$^2$-X  Id

R-A$^1$-Z$^1$-A$^1$-A$^2$-X  Ie

R-A$^1$-A$^1$-Z$^1$-A$^2$-X  If and compounds having four rings of the partial formulae Ig to In:

R-A$^1$-A$^1$-A$^1$-A$^2$-X  Ig

R-A$^1$-Z$^1$-A$^1$-A$^1$-A$^2$-X  Ih

R-A$^1$-A$^1$-Z$^1$-A$^1$-A$^2$-X  Ii

R-A$^1$-A$^1$-A$^1$-Z$^1$-A$^2$-X  Ij

R-A$^1$-Z$^1$-A$^1$-Z$^1$-A$^1$-A$^2$-X  Ik

R-A$^1$-Z$^1$-A$^1$-A$^1$-A$^1$-Z$^1$-A$^2$-X  Il

R-A$^1$-A$^1$-Z$^1$-A$^1$-Z$^1$-A$^2$-X  Im

R-A$^1$-Z$^1$-A$^1$-Z$^1$-A$^1$-Z$^1$-A$^2$-X  In

Of these, in particular those of the partial formulae Ia, Ib, Ic, Id, Ie, If, Ii and Il are preferred.

The preferred compounds of the partial formula Ia comprise those of the partial formulae Iaa to Iah:

R-Phe-Phe-X  Iaa

R-Phe-Cyc-X  Iab

R-Dio-Phe-X  Iac

R-Pyr-Phe-X  Iad

R-Pyd-Phe-X  Iae

R-Cyc-Phe-X  Iaf

R-Cyc-Cyc-X  Iag

R-Che-Phe-X  Iah

Of these, those of the formulae Iaa, Iab, Iac, Iad, Iaf and Iag are particularly preferred.

The preferred compounds of the partial formula Ib comprise those of the partial formulae Iba to Ibm:

R-Phe-CH$_2$CH$_2$-Phe-X  Iba

R-Phe-OCH$_2$-Phe-X  Ibb

R-Cyc-CH$_2$CH$_2$-Phe-X  Ibc

R-Cyc-CH$_2$-CH$_2$-Cyc-X  Ibd

R-Cyc-COO-Phe-X  Ibe

R-Cyc-COO-Cyc-X  Ibf

R-A$^1$-CH$_2$CH$_2$-Phe-X  Ibg

R-A$^1$-CH$_2$CH$_2$-Cyc-X  Ibh

R-A$^1$-CH$_2$O-Phe-X  Ibi

R-A$^1$-CH$_2$-Phe-X  Ibj

R-A$^1$-COO-Phe-X  Ibk

R-A$^1$-OOC-Phe-X  Ibl

R-Che-CH$_2$CH$_2$-Phe-X  Ibm

The preferred compounds of the partial formula Ic comprise those of the partial formulae Ica to Icq:

R-Phe-Phe-Phe-X  Ica

R-Phe-Phe-Cyc-X  Icb

R-Phe-Dio-Phe-X  Icc

R-Cyc-Cyc-Phe-X  Icd

R-Phe-Cyc-Phe-X  Ice

R-Cyc-Cyc-Cyc-X  Icf

R-Pyd-Phe-Phe-X  Icg

| | |
|---|---|
| R-Pyr-Phe-Phe-X | Ich |
| R-Phe-Pyr-Phe-X | Ici |
| R-Cyc-Pyr-Phe-X | Icj |
| R-Cyc-Phe-Phe-X | Ick |
| R-Cyc-Phe-Cyc-X | Icl |
| R-Dio-Phe-Phe-X | Icm |
| R-Che-Phe-Phe-X | Icn |
| R-Phe-Che-Phe-X | Ico |
| R-Che-Cyc-Phe-X | Icp |
| R-Cyc-Che-Phe-X | Icq |

Of these, those of the formulae Ica, Icc, Icd, Ice, Ici and Icj are particularly preferred.

The preferred compounds of the partial formula Id comprise those of the partial formulae Ida to Idn:

| | |
|---|---|
| R-Phe-$Z^1$-Phe-$Z^1$-Phe-X | Ida |
| R-Phe-$Z^1$-Phe-$Z^1$-Cyc-X | Idb |
| R-Phe-$Z^1$-Dio-$Z^1$-Phe-X | Idc |
| R-Cyc-$Z^1$-Cyc-$Z^1$-Phe-X | Idd |
| R-Cyc-$Z^1$-Cyc-$Z^1$-Cyc-X | Ide |
| R-Pyd-$Z^1$-Phe-$Z^1$-Phe-X | Idf |
| R-Phe-$Z^1$-Pyd-$Z^1$-Phe-X | Idg |
| R-Pyr-$Z^1$-Phe-$Z^1$-Phe-X | Idh |
| R-Phe-$Z^1$-Pyr-$Z^1$-Phe-X | Idi |
| R-Phe-$Z^1$-Cyc-$Z^1$-Phe-X | Idj |
| R-Cyc-$Z^1$-Phe-$Z^1$-Cyc-X | Idk |
| R-Cyc-$Z^1$-Phe-$Z^1$-Phe-X | Idl |
| R-Dio-$Z^1$-Phe-$Z^1$-Phe-X | Idm |
| R-Che-$Z^1$-Phe-$Z^1$-Phe-X | Idn |

The preferred compounds of the partial formula Ie comprise those of the partial formulae Iea to Iem:

| | |
|---|---|
| R-Pyr-$Z^1$-Phe-Phe-X | Iea |
| R-Dio-$Z^1$-Phe-Phe-X | Ieb |
| R-Phe-$Z^1$-Phe-Phe-X | Iec |
| R-Cyc-$Z^1$-Phe-Phe-X | Ied |
| R-Cyc-$Z^1$-Phe-Cyc-X | Iee |
| R-Phe-$Z^1$-Cyc-Phe-X | Ief |
| R-Cyc-Z1-Cyc-Phe-X | Ieg |
| R-Cyc-$Z^1$-Cyc-Cyc-X | Ieh |
| R-Phe-$Z^1$-Dio-Phe-X | Iei |
| R-Pyd-$Z^1$-Phe-Phe-X | Iej |
| R-Phe-$Z^1$-Pyr-Phe-X | Iek |
| R-Cyc-$Z^1$-Pyr-Phe-X | Iel |
| R-Phe-$Z^1$-Che-Phe-X | Iem |

The preferred compounds of the partial formula If comprise those of the partial formulae Ifa to Ifr:

| | |
|---|---|
| R-Pyr-Phe-$Z^1$-Phe-X | Ifa |
| R-Pyr-Phe-$OCH_2$-Phe-X | Ifb |
| R-Phe-Phe-$Z^1$-Phe-X | Ifc |
| R-Phe-Phe-OOC-Phe-X | Ifd |
| R-Phe-Phe-$Z^1$-Cyc-X | Ife |
| R-Cyc-Cyc-$Z^1$-Phe-X | Iff |
| R-Cyc-Cyc-$Z^1$-Cyc-X | Ifg |
| R-Cyc-Cyc-$CH_2CH_2$-Phe-X | Ifh |

| | |
|---|---|
| R-Pyd-Phe-Z¹-Phe-X | Ifi |
| R-Dio-Phe-Z¹-Phe-X | Ifj |
| R-Phe-Cyc-Z¹-Phe-X | Ifk |
| R-Phe-Cyc-Z¹-Cyc-X | Ifl |
| R-Phe-Pyd-Z¹-Phe-X | Ifm |
| R-Che-Phe-Z¹-Phe-X | Ifn |
| R-Phe-Che-Z¹-Phe-X | Ifo |
| R-Cyc-Phe-Z¹-Phe-X | Ifp |
| R-Cyc-Phe-OOC-Phe-X | Ifq |
| R-Cyc-Phe-Z¹-Cyc-X | Ifr |

The preferred compounds of the partial formulae Ig to In comprise those of the partial formulae Io to Iy:

| | |
|---|---|
| R-Cyc-Phe-Cyc-Phe-X | Io |
| R-Cyc-Cyc-Phe-Phe-X | Ip |
| R-Cyc-Phe-Phe-Cyc-X | Iq |
| R-A¹-CH₂O-A¹-A¹-Phe-X | Ir |
| R-Cyc-Cyc-Z¹-A¹-Phe-X | Is |
| R-Cyc-Cyc-Z¹-Y¹-Cyc-X | It |
| R-A¹-A¹-A¹-CH₂CH₂-Phe-X | Iu |
| R-Phe-Z¹-Phe-Z¹-Dio-Phe-X | Iv |
| R-Phe-Z¹-Phe-Phe-Z¹-Phe-X | Iw |
| R-A¹-COO-A¹-COO-A¹-Phe-X | Ix |
| R-A¹-A¹-COO-A¹-Z¹-Phe-X | Iy |

In the compounds of the formulae above and below, X is preferably Q-CHF₂ in which Q is alkylene having 2 to 4 carbon atoms and in which a CH₂ group can also be replaced by —O—, —CO—O— or —O—CO—. Furthermore, Q is preferably a single bond, —O—, —S—, —CH₂— and —CO—O—; —O— and —S—are particularly preferred.

If Q is a single bond, those compounds of the formula I are preferred in which X is bound to a cycloaliphatic ring. If Q is —O— or —S—, those compounds of the formula I are preferred in which X is bound to an aromatic ring.

R is preferably alkyl, furthermore alkoxy. Furthermore R is preferably a perfluoroalkyl radical in which fluorine can also be partially replaced by hydrogen. In particular those radicals R of the general formula —CH₂-C$_n$F$_{2n+1}$ and C$_p$F$_{2p+1}$ where n is equal to 1 to 14 and p is equal to 1 to 15 are preferred. A¹ and/or A² are preferably Phe, Cyc, Che, Pyr or Dio. Particularly preferably, A¹ and A² is (sic) Phe or Cyc. Furthermore, those compounds of the formula I are preferred in which, in addition to Phe and/or Cyc, a further ring selected from the group consisting of Che, Pip, Pyr, Pyd, Dio, Dit, Bi, Nap, Dec or Tet is present.

Compounds of the formula I and of all partial formulae in which A¹ and/or A² is (sic) 1,4-phenylene which is monosubstituted or disubstituted by F or monosubstituted by CN are also preferred. These are in particular 2-fluoro-1,4-phenylene, 3-fluoro-1,4-phenylene and 2,3-difluoro-1,4-phenylene and 2-cyano-1,4-phenylene and 3-cyano-1,4-phenylene. Of the F-substituted 1,4-phenylene radicals, in particular

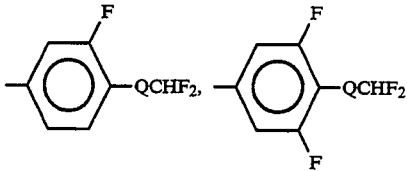

and

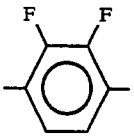

preferred.

If a radical (a) is substituted by F or CN,

is preferred.

Z¹ is preferably a single bond, —CO—O—, —O—CO— and —CH₂CH₂—, the second preference being —CH₂O— and —OCH₂—. Compounds which contain no more than one and at most two linking groups Z¹ (Z¹ not being a single bond) are particularly preferred.

m is preferably 1 or 2.

If R is halogen, R is preferably F, Cl, Br, furthermore also I.

If R is an alkyl radical and/or an alkoxy radical, it can be straight-chain or branched. Preferably it is straight-chain, has 2, 3, 4, 5, 6 or 7 carbon atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7 -oxaoctyl, 2-, 3-, 4-, 5-, 6-, 7 - or 8-oxanonyl, 2-, 3-, 4-, 5-, 6-, 7 -, 8- or 9-oxadecyl.

If R is an alkyl radical in which one CH₂ group has been replaced by —CH=CH—, it can be straight-chain or branched. Preferably, it is straight-chain and has 2 to 10 carbon atoms. Accordingly, it is in particular vinyl, prop- 1 - or prop- 2 -enyl, but- 1 -, - 2 - or but- 3 -enyl, pent-1-, -2-, -3- or pent-4-enyl, hex-1-, -2-, -3-, -4- or hex-5-enyl, hept-1-, -2-, -3-, -4-, -5- or hept-6-enyl, oct-1-, -2 -, -3-, -4-, -5-, -6- or oct-7-enyl, non-1-, -2-, -3-, -4-, -5-, -6-, -7- or non-8-enyl, dec-1-, -2-, -3-, -4-, -5-, -6-, -7-, -8- or dec-9-enyl.

If R is an alkyl radical in which one CH₂ group has been replaced by —O— and one by —CO—, these groups are preferably adjacent. Thus, they contain an acyloxy group —CO—O— or an oxycarbonyl group —O—CO—. Preferably, these are straight-chain and have 2 to 6 carbon atoms. Accordingly, they are in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)butyl.

If R is an alkyl radical in which one CH₂ group has been replaced by unsubstituted or substituted —CH=CH— and one adjacent CH₂ group by CO or CO—O or O—CO—, it can be straight-chain or branched. Preferably, it is straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, 9-methacryloyloxynonyl.

Compounds of the formula I which have wing groups R suitable for polymerization reactions are suitable for the preparation of liquid-crystalline polymers.

Compounds of the formula I containing branched wing groups R can in some cases be important because of better solubility in the conventional liquid-crystalline basis materials, but in particular as chiral doping substances, if they are optically active. Smectic compounds of this type are suitable as components for ferroelectric materials.

Compounds of the formula I which have S_A phases are suitable, for example, for thermally addressed displays.

Branched groups of this type contain, as a rule, not more than one chain branching. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy.

If R is an alkyl radical in which two or more CH₂ groups have been replaced by —O— and/or —CO—O—, it can be straight-chain or branched. Preferably, it is branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2- bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl, 5,5-bis(ethoxycarbonyl)hexyl.

Compounds of the formula I which have wing groups R suitable for polycondensations are suitable for the preparation of liquid-crystalline polycondensation products.

Formula I comprises not only the racemates of these compounds but also the optical antipodes and their mixtures.

Of these compounds of the formula I and the subformulae, those are preferred in which at least one of the radicals contained therein has one of the preferred meanings mentioned.

In the compounds of the formula I, those stereoisomers are preferred in which the rings Cyc and piperidine are trans-1,4-disubstituted. Those of the above-mentioned formulae which contain one or several groups Pyd, Pyr and/or Dio each comprise the two isomers in the 2,5-position.

The 1,4-cyclohexenylene group preferably has the following structures:

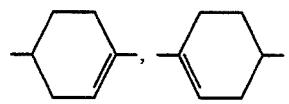

The compounds of the formula I are prepared by methods known per se, such as are described in the literature (for example in the standard works such as Houben-Weyl, Methoden der Organischen Chemie (Methods of Organic Chemistry), Georg-Thieme Verlag, Stuttgart Vol. IX, p. 867 ff.) under reaction conditions which are known and suitable for the reactions mentioned. It is also possible to make use of variations which are known per se and not mentioned in more detail at this point.

The aryldifluoromethyl ethers according to the invention can prepared (sic), for example, by reacting hydroxyaryl compounds with chlorodifluoromethane under reaction conditions which are suitable for the Reimer-Tiemann reaction between phenols and chloroform [T. G. Miller, J. W. Thanassi, J. Org. Chem. 25, 2009 (1960)].

The etherification can be carried out in known manner in aprotic, strongly polar solvents (JP-OS 59/157,041) and in aqueous or even in almost anhydrous media, for example, by carrying out the formation of alcohol in aqueous-organic phase (for example tetrahydrofuran/water), but removing most of the water azeotropically before the actual etherification.

Difluoroalkylaryl ethers according to the invention can, for example, also be prepared, for example, by reacting the corresponding nitro- or fluorobenzenes which additionally carry at least one electron-withdrawing substituent directly with alkali metal difluoroalkoxy compounds, in which F or $NO_2$ is substituted by the difluoroalkoxy radical [J. P. Idoux et al., J. Org. Chem. 50, 1976 (1985)].

Difluoromethyl compounds of the formula I can be prepared, for example, by reacting aldehydes with dialkylaminosulfur trifluoride, for example DAST (diethylamino sulfurtrifluoride) [W. J. Middleton, J. Org. Chem. 40, 574 (1975)].

Difluoromethylthio compounds can be prepared by the same method as difluoromethoxy compounds (for example according to L. N. Sedova et al., Zh. Org. Khim. 6, (1970) 568).

If desired, the starting materials can also be formed in situ in such a manner that they are not isolated from the reaction mixture but immediately reacted further to give the compounds of the formula I.

Thus, the compounds of the formula I can be prepared by reducing a compound which otherwise corresponds to the formula I, but contains one or more reducible groups and/or C-C bonds instead of the hydrogen atoms.

Suitable reducible groups are preferably carbonyl groups, in particular keto groups, furthermore, for example, free or esterified hydroxyl groups or aromatically bound halogen atoms. Preferred starting materials for the reduction have the formula I, but can contain a cyclohexene ring or cyclohexanone ring instead of a cyclohexane ring and/or a —CH=CH— group instead of a —$CH_2CH_2$— group and/or a —CO— group instead of a —$CH_2$ group and/or a free or functionally (for example in the form of its p-toluenesulfonate) modified OH group instead of a hydrogen atom.

The reduction can be carried out, for example, by catalytic hydrogenation at temperatures between about 0° and about 200° and pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable catalysts are advantageously noble metals such as Pt or Pd, which can be used in the form of oxides (for example $PtO_2$, PdO) on a support (for example Pd on carbon, calcium carbonate or strontium carbonate) or in finely divided form.

Ketones can also be reduced by the methods of Clemmensen (using zinc, amalgamated zinc or tin and hydrochloric acid, advantageously in aqueous-alcoholic solution or in heterogeneous phase using water/toluene at temperatures between about 80° and 120°) or Wolff-Kishner (using hydrazine, advantageously in the presence of alkali such as KOH or NaOH in a high-boiling solvent such as diethylene glycol or triethylene glycol at temperatures between about 100° and 200°) to give the corresponding compounds of the formula I containing alkyl groups and/or —$CH_2CH_2$— bridges.

Another possibility are reductions using complex hydrides. For example, arylsulfonyloxy groups can be removed reductively using $LiAlH_4$, in particular p-toluenesulfonyloxymethyl groups can be reduced to methyl groups, advantageously in an inert solvent such as diethyl ether or THF at temperatures between about 0° and 100°. Double bonds can be hydrogenated using $NaBH_4$ or tributyltin hydride in methanol.

Compounds of the formula I which otherwise correspond to the formula I, but have 1,4-cyclohexenylene radicals instead of 1,4-phenylene radicals, can be oxidized, for example, with DDQ (dichlorodicyanobenzoquinone) in a suitable solvent.

Esters of the formula I can also be obtained by esterification of the corresponding carboxylic acids (or their reactive derivatives) with alcohols or phenols (or their reactive derivatives) or by the DCC method (DCC=dicyclohexylcarbodiimide).

The corresponding carboxylic acids and alcohols or phenols are known or can be prepared in analogy to known processes.

Thiophenols can be prepared, for example, by reacting the corresponding benzene derivatives with chlorosulfonic acid and then reducing the product, for example using zinc/dilute hydrochloric acid, or reacting the corresponding phenol derivatives with dimethylcarbamoyl chloride and then rearranging the product, as described in DE 3,434,335.

Suitable reactive derivatives of the carboxylic acids mentioned are in particular acid halides, in particular the chlorides and bromides, furthermore the anhydrides, for example even mixed anhydrides, azides or esters, in particular alkyl esters having 1-4 carbon atoms in the alkyl group.

Suitable reactive derivatives of the alcohols and phenols mentioned are in particular the corresponding metal alcoholates or phenolates, preferably of an alkali metal such as sodium or potassium.

The esterification is advantageously carried out in the presence of an inert solvent. Very suitable for this purpose are in particular ethers such as, for example, diethyl ether, di-n-butyl ether, THF, dioxane or anisole, ketones such as, for example, acetone, butanone or cyclohexanone, amides such as, for example, DMF or hexamethylphosphoric triamide, hydrocarbons such as, for example, benzene, toluene or xylene, halogenated hydrocarbons such as, for example, carbon tetrachloride, dichloromethane or tetrachloroethylene and sulfoxides such as, for example, dimethyl sulfoxide or sulfolane.

In a further process for the preparation of the compounds of the formula I, an aryl halide is reacted with an olefin in the presence of a tertiary amine and a palladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the successful completion of the coupling reaction, such as, for example, triethylamine, are also suitable as solvents. Examples of suitable palladium catalysts are palladium salts, in particular Pd(II) acetate, in combination with organic phosphorus(III) compounds such as, for example, triarylphosphanes. This reaction can be carried out in the presence or absence of an inert solvent at temperatures between about 0° and 150°, preferably between 20° and 100°; examples of suitable solvents are nitriles such as acetonitrile or hydrocarbons such as benzene or toluene. Many of the aryl halides and olefins used as starting materials are commercially available or can be prepared by processes known from the literature, for example by halogenation of the corresponding parent compounds or by elimination reactions of the corresponding alcohols or halides.

For example, stilbene derivatives can be prepared in this manner. The stilbenes can also be prepared by reaction of a 4-substituted benzaldehyde with the corresponding phosphorus ylide according to Wittig. However, it is also possible to prepare tolans of the formula I by using monosubstituted acetylene instead of the olefin (Synthesis 627 (1980) or Tetrahedron Lett. 27, 1171 (1986)).

Furthermore, aromatics can be coupled by reacting aryl halides with aryltin compounds. Preferably, these reactions are carried out with the addition of a catalyst such as, for example, a palladium(0) complex in inert solvents such as hydrocarbons at high temperatures, for example in boiling xylene, under a protective gas.

Couplings of alkyinyl compounds with aryl halides can be carried out analogously to the process described by A. O. King, E. Negishi, F. J. Villani and A. Silveira in J. Org. Chem. 43, 358 (1978).

Tolans of the formula I can also be prepared via the Fritsch-Buttenberg-Wiechell rearrangement (Ann. 279, 319, 332, 1984), in which 1,1-diaryl-2-halogenoethylenes are rearranged to diarylacetylenes in the presence of strong bases.

Tolanes of the formula I can also be prepared by bromination of the corresponding stilbenes, followed by dehydrohalogenation. It is possible to use the variations of this reaction which are known per se but not mentioned here in more detail.

Nitriles of the formula I can be prepared by dehydrating the corresponding amides, for example those which have a $CONH_2$ group instead of the radical CN. The amides are obtainable, for example, from the corresponding esters or acid halides by reaction with ammonia. Examples of suitable dehydrating agents are inorganic acid chlorides such as $SOCl_2$, $PCl_3$, $PCl_5$, $POCl_3$, $SO_2Cl_2$, $COCl_2$, furthermore $P_2O_5$, $P_2S_5$, $AlCl_3$ (for example as double salt with NaCl), aromatic sulfonic acids and sulfonyl halides. This reaction can be carried out in the presence or absence of an inert solvent at temperatures between about 0° and 150°; examples of suitable solvents are bases such as pyridine or triethylamine, aromatic hydrocarbons such as benzene, toluene or xylene or amides such as DMF.

The abovementioned nitriles of the formula I can also be prepared by reacting the corresponding acid halides, preferably the chlorides, with sulfamide, advantageously in an inert solvent such as, for example, tetramethylene sulfone at temperatures between about 80° and 150°, preferably at 120°. After conventional work-up, the nitriles can be isolated directly.

Ethers of the formula I are available by etherification of the corresponding hydroxy compounds, preferably of the corresponding phenols, in which the hydroxy compound is advantageously first converted into a corresponding metal derivative, for example converted into a corresponding alkali metal alcoholate or alkali metal phenolate by treatment with NaH, $NaNH_2$, NaOH, KOH, $Na_2CO_3$ or $K_2CO_3$. This derivative can then be reacted with the corresponding alkyl halide, alkyl sulfonate or dialkyl sulfate, advantageously in an inert solvent such as, for example, acetone, 1,2-dimethoxyethane, DMF or dimethyl sulfoxide or even with an excess of aqueous or aqueous-alcoholic NaOH or KOH at temperatures between about 20° and 100°.

The nitriles of the formula I can also be prepared by reacting the corresponding chlorine, bromine or iodine compounds of the formula I with a cyanide, preferably with a metal cyanide such as, for example, NaCN, KCN or $Cu_2(CN)_2$, for example in the presence of pyridine in an inert solvent such as, for example, DMF or N-methylpyrrolidone at temperatures between 20° and 200°.

Compounds of the formula I in which $A^1$ is substituted by at least one F atom and/or one CN group can also be obtained from the corresponding diazonium salts by exchange of the diazonium group for a fluorine atom or for a CN group, for example by the methods of Schiemann or Sandmeyer.

Dioxane derivatives or dithiane derivatives of the formula I are advantageously prepared by reaction of the corresponding aldehyde (or of one of its reactive derivatives) with a suitable 1,3-diol (or one of its reactive derivatives) or a suitable 1,3-dithiol, preferably in the presence of an inert solvent such as, for example, benzene or toluene and/or a catalyst, for example a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

Some of the aldehydes and 1,3-diols or 1,3-dithiols mentioned and their reactive derivatives are known and others can be prepared without difficulties by standard processes of organic chemistry from compounds known from the literature. For example, the aldehydes are available by oxidation of the corresponding alcohols or by reduction of nitriles or the corresponding carboxylic acids or their derivatives, the diols by reduction of the corresponding diesters and the dithiols by reaction of the corresponding dihalides with NaSH.

The liquid-crystalline media according to the invention preferably contain, in addition to one or more compounds according to the invention, as further components 2 to 40, in particular 4 to 30 components. Very particularly preferably, these media contain, in addition to one or more compounds according to the invention, 7 to 25 components. These further components are preferably selected from nematic or nematogenic (monotropic or isotropic) substances, in particular substances from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexylphenyl cyclohexanecarboxylates, cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl-or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, halogenated or unhalogenated stilbenes, benzyl phenyl ethers, tolanes and substituted cinnamic acids. The 1,4-phenylene groups in these compounds can also be fluorinated.

The most important compounds which are suitable as further components of media according to the invention can be characterized by formulae 1, 2, 3, 4 and 5:

R'-L-E-R"   1

R'-L-COO-E-R"  2

R'-L-OOC-E-R"  3

R'-L-CH₂CH₂-E-R"  4

R'-L-C-C-E-R"  5

In the formulae 1, 2, 3, 4 and 5, L and E, which can be identical or different, are each, independently of one another, a divalent radical from the group consisting of -Phe-, -Cyc-, -Phe-Phe-, -Phe-Cyc-, -Cyc-Cyc-, -Pyr, -Dio-, -G-Phe- and -G-Cyc- and their mirror images, in which Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe-Cyc. Preferably, the media according to the invention contain one or more components selected from the compounds of the formulae 1, 2, 3, 4 and 5, in which L and E are selected from the group consisting of Cyc, Phe and Pyr and simultaneously one or more components are selected from the compounds of the formulae 1, 2, 3, 4 and 5, in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and possibly one or more components are selected from the compounds of the formulae 1, 2, 3, 4 and 5, in which the radicals L and E are selected from the group consisting of -Phe-Cyc-, -Cyc-Cyc-, -G-Phe- and -G-Cyc-.

R' and R" in the compounds of the partial formulae 1a, 2a, 3a, 4a and 5a are each, independently of one another, alkyl, alkenyl, alkoxy, alkenyloxy or alkanoyloxy having up to 8 carbon atoms. In most of these compounds, R' and R" are different from one another and one of these radicals is in most cases alkyl or alkenyl. In the compounds of the partial formulae 1b, 2b, 3b, 4b and 5b, R" is —CN, —CF₃, F, Cl or —NCS; in these formulae, R has the meaning mentioned in the compounds of the partial formulae 1a to 5a and is preferably alkyl or alkenyl. However, other variations of the substituents intended for the compounds of the formulae 1, 2, 3, 4 and 5 are common. Many of these substances or even mixtures thereof are commercially available. All these substances are available by methods known from the literature or analogously to those methods.

The media according to the invention preferably contain, in addition to the components from the group of compounds 1a, 2a, 3a, 4a and 5a (group 1), also components from the group of compounds 1b, 2b, 3b, 4b and 5b (group 2), the relative proportions of which are preferably as follows:

Group 1: 20 to 90%, in particular 30 to 90%,
Group 2: 10 to 80%, in particular 10 to 50%,
the sum of the relative proportions of the compounds according to the invention and the compounds from groups 1 and 2 adding up to 100%.

The media according to the invention preferably contain 1 to 40%, in particular preferably 5 to 30%, of compounds according to the invention. Further preference is given to media containing more than 40%, in particular 45 to 90%, of compounds according to the invention. The media preferably contain three, four or five compounds according to the invention.

The media according to the invention are prepared in a manner customary per se. As a rule, the components are dissolved in one another, advantageously at elevated temperature. By means of suitable additives, the liquid-crystalline phases according to the invention can be modified in such a manner that they can be used in all previously known types of liquid crystal display elements. This type of additive is known to one skilled in the art and has been described in detail in the literature (H. Kelker/R. Hatz, Handbook of Liquid Crystals, Verlag Chemie, Weinheim, 1980). For example, pleochroitic dyes to prepare coloured guest-host systems or substances to change the dielectric anisotropy, the viscosity and/or the orientation of the nematic phases can be added.

The examples which follow are intended to illustrate the invention without limiting it. Above and below, percentages are by weight. All temperatures are given in degrees centigrade. m.p. denotes melting point and c.p. =clear point. Furthermore, C denotes crystalline state, N nematic phase, S smectic phase and I isotropic phase. The data between these symbols represent the transition temperatures. $\Delta n$ denotes optical anisotropy (589 nm, 20° C.) and viscosity (mm²/sec) was determined at 20° C.

"Usual work-up" means: if desired, water is added, the product is extracted with methylene chloride, diethyl ether or toluene, the organic phase is separated off, dried, evaporated, and the product is purified by distillation under reduced pressure or crystallization and/or chromatography. The following abbreviations are used:

DAST diethylaminosulfur trifluoride
DCC dicyclohexylcarbodiimide
DDQ dichlorodicyanobenzoquinone
DIBALH diisobutylaluminum hydride
KOT potassium t-butoxide
THF tetrahydrofuran
pTSOH p-toluenesulfonic acid

EXAMPLE 1

4-Difluoromethoxy-4'-octoxy-biphenyl

A mixture of 20 g of 4-hydroxy-4'-octyloxybiphenyl, 13.6 g of NaOH, 100 ml of water and 150 ml of dioxane is heated to 70° C. with stirring. 10 g of chlorodifluoromethane are passed into the cooled two-phase mixture with vigorous stirring. The reaction mixture is poured into water, and the product is extracted with petroleum ether. The organic phase is dried over Na₂SO₄, evaporated, and the residue is filtered through a short silica gel column using petroleum ether as eluent. The product is recrystallized from acetonitrile. Colourless crystals are obtained. m.p.: 104° C., c.p.: 20° C. (extrapolated), $\Delta n$=0.093, viscosity: 17

The following were prepared analogously:
4-difluoromethoxy-4'-methoxy-biphenyl
4-difluoromethoxy-4'-ethoxy-biphenyl
4-difluoromethoxy-4'-propoxy-biphenyl
4-difluoromethoxy-4'-butoxy-biphenyl, m.p.: 122° C., $\Delta n$=0.146

4-difluoromethoxy-4'-pentoxy-biphenyl
4-difluoromethoxy-4'-hexoxy-biphenyl
4-difluoromethoxy-4'-heptoxy-biphenyl
4-difluoromethoxy-4'-nonoxy-biphenyl
4-difluoromethoxy-4'-decoxy-biphenyl
4-difluoromethoxy-4'-methyl-biphenyl
4-difluoromethoxy-4'-ethyl-biphenyl
1-(4-difluoromethoxyphenyl)-4-ethyl-bicyclo[2.2.2]octane
4-difluoromethoxy-4'-propyl-biphenyl, m.p.: 84° C., c.p. (extrapolated) : −30° C. viscosity: 6
4-difluoromethoxy-4-butyl-biphenyl
4-difluoromethoxy-4'-pentyl-biphenyl
4-difluoromethoxy-4'-hexyl-biphenyl
4-difluoromethoxy-4'-heptyl-biphenyl
4-difluoromethoxy-4'-nonyl-biphenyl
4-difluoromethoxy-4'-decyl-biphenyl
1-propyl-3-(4-difluoromethoxyphenyl-4'-yl)-cyclobutane
6-(4-difluoromethoxyphenyl)-2-methyl-naphthalene
6-(4-difluoromethoxyphenyl)-2-methyl-1,2,3,4-tetrahydronaphthalene
difluoromethoxy-4-(trans-4-ethylcyclohexyl)-benzene
difluoromethoxy-4-(trans-4-propylcyclohexyl)-benzene
m.p.: −15° C., c.p.: −40° C. (extrapolated), Δn=0.035, viscosity: 5;
difluoromethoxy-4-( trans-4-butylyclohexyl )-benzene (sic)
m.p.: 8° C., c.p.: −30° C. (extrapolated), Δn=0.043, viscosity: 6;
difluoromethoxy-4-(trans-4-pentylcyclohexyl)-benzene
m.p.: 1° C., c.p.: −17° C., Δn=0.058, viscosity: 7;
difluoromethoxy-4-(trans-4-hexylcyclohexyl)-benzene
difluoromethoxy-4-(trans-4-heptylcyclohexyl)-benzene
difluoromethoxy-4-(trans-4-octylcyclohexyl)-benzene
difluoromethoxy-4-(trans-4-nonylcyclohexyl)-benzene
difluoromethoxy-4-(trans-4-decylcyclohexyl)-benzene
4-difluoromethoxy-2',3'-difluoro-4'-methoxy-biphenyl
4-difluoromethoxy-2',3'-difluoro-4'-ethoxy-biphenyl
4-difluoromethoxy-2',3'-difluoro-4'-propoxy-biphenyl
4-difluoromethoxy-2',3'-difluoro-4'-butoxy-biphenyl
4-difluoromethoxy-2',3'-difluoro-4'-pentoxy-biphenyl
4-difluoromethoxy-2',3'-difluoro-4'-hexoxy-biphenyl
4-difluoromethoxy-2',3'-difluoro-4'-heptoxy-biphenyl
4-difluoromethoxy-2',3'-difluoro-4'-octoxy-biphenyl
4-difluoromethoxy-2',3'-difluoro-4'-nonoxy-biphenyl
4-difluoromethoxy-2',3'-difluoro-4'-decoxy-biphenyl
4-difluoromethoxy-2',3'-difluoro-4'-methyl-biphenyl
4-difluoromethoxy-2',3'-difluoro-4'-ethyl-biphenyl
4-difluoromethoxy-2',3'-difluoro-4'-propyl-biphenyl
4-difluoromethoxy-2',3'-difluoro-4'-butyl-biphenyl
4-difluoromethoxy-2',3'-difluoro-4'-pentyl-biphenyl
4-difluoromethoxy-2',3'-difluoro-4'-hexyl-biphenyl
4-difluoromethoxy-2',3'-difluoro-4'-heptyl-biphenyl
4-difluoromethoxy-2',3'-difluoro-4'-octyl-biphenyl
4-difluoromethoxy-2',3'-difluoro-4'-nonyl-biphenyl
4-difluoromethoxy-2',3'-difluoro-4'-decyl-biphenyl
4-difluoromethoxy-4'-cyano-3'-fluorobiphenyl
4-difluoromethoxy-4'-methyl-terphenyl
4-difluoromethoxy-4'-ethyl-terphenyl
4-difluoromethoxy-4'-propyl-terphenyl
4-difluoromethoxy-4'-butyl-terphenyl
4-difluoromethoxy-4'-pentyl-terphenyl, m.p.: 223° C., c.p.: 241° C.
4-difluoromethoxy-4'-hexyl-terphenyl
4-difluoromethoxy-4'-heptyl-terphenyl
4-difluoromethoxy-4'-octyl-terphenyl
4-difluoromethoxy-4'-nonyl-terphenyl
4-difluoromethoxy-4'-decyl-terphenyl
4-difluoromethoxy-4'-(trans-4-methylcyclohexyl)-biphenyl
4-difluoromethoxy-4'-(trans-4-ethylcyclohexyl)-biphenyl
4-difluoromethoxy-4'-(trans-4-propylcyclohexyl)-biphenyl,
m.p.: 82° C., c.p.: 169.4° C., Δn=0.174
4-difluoromethoxy-4'-(trans-4-butylcyclohexyl)-biphenyl
4-difluoromethoxy-4'-(trans-4-pentylcyclohexyl)-biphenyl,
m.p.: 67° C., c.p.: 161.8° C., Δn=0.115
4-difluoromethoxy-4'-(trans -4 -hexylcyclohexyl)-biphenyl
4-difluoromethoxy-4'-(trans-4-heptylcyclohexyl)-biphenyl
4-difluoromethoxy-4'-(trans -4 -octylcyclohexyl)-biphenyl
4-difluoromethoxy-4'-(trans -4 - nonylcyclohexyl)-biphenyl
4-difluoromethoxy-4'-(trans -4 -decylcyclohexyl)-biphenyl
4-methyl-4'-(4-difluoromethoxyphenyl)-trans, trans-bicyclohexyl
4-trifluoromethyl-4'-(4-difluoromethoxyphenyl)-trans,trans-bicyclohexyl
4-ethyl -4'-(4 -difluoromethoxyphenyl)-trans, trans-bicyclohexyl
4-propyl-4'-(4-difluoromethoxyphenyl)-trans, trans-bicyclohexyl, m.p.: 39° C., c.p.: −148.6° C., Δn=0.088, viscosity: 16
4-isopropyl-4'-(4-difluoromethoxyphenyl)-trans,-transbicyclohexyl
4-butyl-4'-(4-difluoromethoxyphenyl)-trans,trans-bicyclohexyl
4-methoxyethyl-4'-(4-difluoromethoxyphenyl)-trans,-transbicyclohexyl
4-pentyl-4'-(4-difluoromethoxyphenyl)-trans,trans-bicyclohexyl
4-hexyl-4'-(4-difluoromethoxyphenyl)-trans,trans-bicyclohexyl
4-heptyl-4'-(4-difluoromethoxyphenyl)-trans,trans-bicyclohexyl
4-octyl-4'-(4-difluoromethoxyphenyl)-trans,trans-bicyclohexyl
4-nonyl-4'-(4-difluoromethoxyphenyl)-trans,trans-bicyclohexyl
4-decyl-4'-(4-difluoromethoxyphenyl)-trans,trans-bicyclohexyl
1-(4-difluoromethoxyphenyl)-4-(trans-4-methylcyclohexyl)cyclohexene
1-(4-difluoromethoxyphenyl)-4-(trans-4-ethylcyclohexyl)cyclohexene
1-(4-difluoromethoxyphenyl)-4-(trans-4-propylcyclohexyl)cyclohexene
1-(4-difluoromethoxyphenyl)-4-(trans-4-butylcyclohexyl)cyclohexene 1-(4-difluoromethoxyphenyl)-4-(trans-4-pentylcyclohexyl)cyclohexene
1-(4-difluoromethoxyphenyl)-4-(trans-4-hexylcyclohexyl)cyclohexene
1-(4-difluoromethoxyphenyl)-4-(trans-4-heptylcyclohexyl)cyclohexene
1-(4-difluoromethoxyphenyl)-4-(trans-4-octylcyclohexyl)cyclohexene
1-(4-difluoromethoxyphenyl)-4-(trans-4-nonylcyclohexyl)cyclohexene
1-(4-difluoromethoxyphenyl)-4-(trans-4-decylcyclohexyl)cyclohexene
1-(4-difluoromethoxyphenyl)-trans-4-(1-methylcyclohexen-4-yl)-cyclohexane
1-(4-difluoromethoxyphenyl)-trans-4-(1-ethylcyclohexen-4-yl)-cyclohexane
1-(4-difluoromethoxyphenyl)-trans-4-(1-propylcyclohexen-4-yl)-cyclohexane
1-(4-difluoromethoxyphenyl)-trans-4-(1-butylcyclohexen-4-yl)-cyclohexane
1(4-difluoromethoxyphenyl)-trans-4-(1-pentylcyclohexen-4-yl)-cyclohexane
1-(4-difluoromethoxyphenyl)-trans-4-(1-hexylcyclohexen-4-yl)-cyclohexane
1-(4-difluoromethoxyphenyl)-trans-4-(1-heptylcyclohexen-4-yl)-cyclohexane
1-(4-difluoromethoxyphenyl)-trans-4-(1-octylcyclohexen-4-yl)-cyclohexane
1-(4-difluoromethoxyphenyl)-trans-4-(1-nonylcyclohexen-4-yl)-cyclohexane
1-(4-difluoromethoxyphenyl)-trans-4-(1-decylcyclohexen-4-yl)-cyclohexane
4-methyl-4'-(3-fluoro-4-difluoromethoxyphenyl)-trans,trans-bicyclohexyl
4-ethyl-4'-(3-fluoro-4-difluoromethoxyphenyl)-trans,trans-bicyclohexyl
4-propyl-4'-(3,5-difluoro-4-difluoromethoxyphenyl)-trans,trans-bicyclohexyl
4-propyl-4'-(3-fluoro-4-difluoromethoxyphenyl)-trans,trans-bicyclohexyl, m.p.: 33° C., c.p.: 144° C., Δn=0.106
4-butyl-4'-(3-fluoro-4-difluoromethoxyphenyl)-trans,trans-bicyclohexyl
4-pentyl-4'-(3-fluoro-4-difluoromethoxyphenyl)-trans,trans-bicyclohexyl
4-hexyl-4'-(3-fluoro-4-difluoromethoxyphenyl)-trans,trans-bicyclohexyl
4-heptyl-4'-(3-fluoro-4-difluoromethoxyphenyl)-trans,trans-bicyclohexyl
4-octyl-4'-(3-fluoro-4-difluoromethoxyphenyl)-trans,trans-bicyclohexyl
4-nonyl-4'-(3-fluoro-4-difluoromethoxyphenyl)-trans,trans-bicyclohexyl
4-decyl-4'-(3-fluoro-4-difluoromethoxyphenyl)-trans,trans-bicyclohexyl The following were prepared analogously from the corresponding thiols:
4-difluoromethylthio-4'-methyl-biphenyl
4-difluoromethylthio-4'-ethyl-biphenyl
4-difluoromethylthio-4'-propyl-biphenyl
4-difluoromethylthio-4'-butyl-biphenyl
4-difluoromethylthio-4'-pentyl-biphenyl
4-difluoromethylthio-4'-hexyl-biphenyl
4-difluoromethylthio-4'-heptyl-biphenyl
4-difluoromethylthio-4'-octyl-biphenyl
4-difluoromethylthio-4'-nonyl-biphenyl
4-difluoromethylthio-4'-decyl-biphenyl
difluoromethylthio-4-(trans-4-methylcyclohexyl)-benzene
difluoromethylthio-4-(trans-4-ethylcyclohexyl)-benzene
difluoromethylthio-4-(trans-4-propylcyclohexyl)-benzene
difluoromethylthio-4-(trans-4-butylcyclohexyl)-benzene
difluoromethylthio-4-(trans-4-pentylcyclohexyl)-benzene
difluoromethylthio-4-(trans-4-hexylcyclohexyl)-benzene
difluoromethylthio-4-(trans-4-heptylcyclohexyl)-benzene
difluoromethylthio-4-(trans-4-octylcyclohexyl)-benzene
difluoromethylthio-4-(trans-4-nonylcyclohexyl)-benzene
difluoromethylthio-4-(trans-4-decylcyclohexyl)-benzene
4-difluoromethylthio-4'-(trans-4-methylcyclohexyl)-biphenyl
4-difluoromethylthio-4'-(trans-4-ethylcyclohexyl)-biphenyl
4-difluoromethylthio-4'-(trans-4-methylcyclohexyl)-biphenyl
4-difluoromethylthio-4'-(trans-4-propylcyclohexyl)-biphenyl
4-difluoromethylthio-4'-(trans-4-butylcyclohexyl)-biphenyl
4-difluoromethylthio-4'-(trans-4-pentylcyclohexyl)-biphenyl
4-difluoromethylthio-4'-(trans-4-hexylcyclohexyl)-biphenyl
4-difluoromethylthio-4'-(trans-4-heptylcyclohexyl)-biphenyl
4-difluoromethylthio-4'-(trans-4-octylcyclohexyl)-biphenyl
4-difluoromethylthio-4'-(trans-4-nonylcyclohexyl)-biphenyl
4-difluoromethylthio-4'-(trans-4-decylcyclohexyl)-biphenyl

EXAMPLE 2

Difluoromethoxy-(5-propyl-1,3-dioxan-2-yl)-benzene (sic)

17.2 g of p-difluoromethoxybenzaldehyde (commercially available from Fluorochem. Ltd. (GB)), 10.4 g of ethylpropanediol and 0.2 g of p-TsOH are heated to boiling for 2 hours in 100 ml of toluene. After evaporation of the solvent, the mixture is worked up as usual.

The following were prepared analogously:
difluoromethoxy-(5-ethyl-1,3-dioxan-2-yl)-benzene (sic)
difluoromethoxy-(5-butyl-1,3-dioxan-2-yl)-benzene (sic)
difluoromethoxy-(5-pentyl-1,3-dioxan-2-yl)-benzene (sic)
difluoromethoxy-(5-hexyl-1,3-dioxan-2-yl)-benzene (sic)
difluoromethoxy-(5-heptyl-1,3-dioxan-2-yl)-benzene (sic)
difluoromethoxy-(5-octyl-1,3-dioxan-2-yl)-benzene (sic)
difluoromethoxy-(5-nonyl-1,3-dioxan-2-yl)-benzene (sic)

difluoromethoxy-(5-decyl-1,3-dioxan-2-yl)-benzene (sic)
difluoromethoxy-4-[5-(trans-4-ethylcyclohexyl)-1,3-dioxan-2-yl]-benzene
difluoromethoxy-4-[5-(trans-4-propylcyclohexyl)-1,3-dioxan-2-yl]-benzene
difluoromethoxy-4-[5-(trans-4-butylcyclohexyl)-1,3-dioxan-2-yl]-benzene
difluoromethoxy-4-[5-(trans-4-pentylcyclohexyl)-1,3-dioxan-2-yl]-benzene
difluoromethoxy-4-[5-(trans-4-hexylcyclohexyl)-1,3-dioxan-2-yl]-benzene
difluoromethoxy-4-[5-(trans-4-heptylcyclohexyl)-1,3-dioxan-2-yl]-benzene
difluoromethoxy-4-[5-(trans-4-octylcyclohexyl)-1,3-dioxan-2-yl]-benzene
difluoromethoxy-4-[5-(trans-4-nonylcyclohexyl)-1,3-dioxan-2-yl]-benzene
difluoromethoxy-4-[5-(trans-4-decylcyclohexyl)-1,3-dioxan-2-yl]-benzene

EXAMPLE 3

Difluoromethoxy-4-(5-heptyl-1,3-pyrimidin-2-yl)-benzene

A mixture of 22.2 g of p-difluoromethoxybenzimidamide hydrochloride (available from the nitrile via the corresponding ethyl benzimidate hydrochloride) and 31.8 g of heptylmalonedialdehyde bis(diethyl) acetal is stirred at 150° C. for 15 hours. After cooling, the mixture is worked up as usual. m.p.: 26° C., c.p.: 32° C., $\Delta n$: 0.112, viscosity: 16.

The following were prepared analogously:
difluoromethoxy-4-(5-methyl-1,3-pyrimidin-2-yl)-benzene
difluoromethoxy-4-(5-ethyl-1,3-pyrimidin-2-yl)-benzene
difluoromethoxy-4-(5-propyl-1,3-pyrimidin-2-yl)-benzene,
m.p.: 41° C., c.p. (extrapolated): 0° C., $\Delta n = 0.150$, viscosity: 14
difluoromethoxy-4-(5-butyl-1,3-pyrimidin-2-yl)-benzene
difluoromethoxy-4-(5-pentyl-1,3-pyrimidin-2-yl)-benzene,
m.p.: 21° C., c.p.: 26° C., $\Delta n$: 0.13, viscosity: 14
difluoromethoxy-4-(5-hexyl-1,3-pyrimidin-2-yl)-benzene
difluoromethoxy-4-(5-octyl-1,3-pyrimidin-2-yl)-benzene
difluoromethoxy-4-(5-nonyl-1,3-pyrimidin-2-yl)-benzene
difluoromethoxy-4-(5-decyl-1,3-pyrimidin-2-yl)-benzene
difluoromethoxy-4-(5-methoxy-1,3-pyrimidin-2-yl)-benzene
difluoromethoxy-4-(5-ethoxy-1,3-pyrimidin-2-yl)-benzene
difluoromethoxy-4-(5-propoxy-1,3-pyrimidin-2-yl)-benzene
difluoromethoxy-4-(5-butoxy-1,3-pyrimidin-2-yl)-benzene
difluoromethoxy-4-(5-pentoxy-1,3-pyrimidin-2-yl)-benzene
difluoromethoxy-4-(5-hexoxy-1,3-pyrimidin-2-yl)-benzene
difluoromethoxy-4-(5-heptoxy-1,3-pyrimidin-2-yl)-benzene
difluoromethoxy-4-(5-octoxy-1,3-pyrimidin-2-yl)-benzene
difluoromethoxy-4-(5-nonoxy-1,3-pyrimidin-2-yl)-benzene
difluoromethoxy-4-(5-decoxy-1,3-pyrimidin-2-yl)-benzene
difluoromethoxy-4-[5-(trans-4-methylcyclohexyl)-1,3-pyrimidin-2-yl]-benzene
difluoromethoxy-4-[5-(trans-4-ethylcyclohexyl)-1,3-pyrimidin-2-yl]-benzene
difluoromethoxy-4-[5-(trans-4-propylcyclohexyl)-1,3-pyrimidin-2-yl]-benzene
difluoromethoxy-4-[5-(trans-4-butylcyclohexyl)-1,3-pyrimidin-2-yl]-benzene
difluoromethoxy-4-[5-(trans-4-pentylcyclohexyl)-1,3-pyrimidin-2-yl]-benzene
difluoromethoxy-4-[5-(trans-4-hexylcyclohexyl)-1,3-pyrimidin-2-yl]-benzene
difluoromethoxy-4-[5-(trans-4-heptylcyclohexyl)-1,3-pyrimidin-2-yl]-benzene
difluoromethoxy-4-[5-(trans-4-octylcyclohexyl)-1,3-pyrimidin-2-yl]-benzene
difluoromethoxy-4-[5-(trans-4-nonylcyclohexyl)-1,3-pyrimidin-2-yl]-benzene
difluoromethoxy-4-[5-(trans-4-decylcyclohexyl)-1,3-pyrimidin-2-yl]-benzene
difluoromethoxy-4-[5-(2-(trans-4-methylcyclohexyl)-ethyl)-1,3-pyrimidin-2-yl]-benzene
difluoromethoxy-4-[5-(2-(trans-4-ethylcyclohexyl)-ethyl)-1,3-pyrimidin-2-yl]-benzene
difluoromethoxy-4-[5-(2-(trans-4-propylcyclohexyl)ethyl)-1,3-pyrimidin-2-yl]-benzene
difluoromethoxy-4-[5-(2-(trans-4-butylcyclohexyl)-ethyl)-1,3-pyrimidin-2-yl]-benzene
difluoromethoxy-4-[5-(2-(trans-4-pentylcyclohexyl)-ethyl)-1,3-pyrimidin-2-yl]-benzene
difluoromethoxy-4-[5-(2-(trans-4-hexylcyclohexyl)-ethyl)-1,3-pyrimidin-2-yl]-benzene
difluoromethoxy-4-[5-(2-(trans-4-heptylcyclohexyl)-ethyl)-1,3-pyrimidin-2-yl]-benzene
difluoromethoxy-4-[5-(2-(trans-4-octylcyclohexyl)-ethyl)-1,3-pyrimidin-2-yl]-benzene
difluoromethoxy-4-[5-(2-(trans -4 -nonylcyclohexyl)-ethyl)-1,3-pyrimidin-2-yl]-benzene
difluoromethoxy-4-[5-(2-(trans-4-decylcyclohexyl)-ethyl)-1,3-pyrimidin-2-yl]-benzene Using 4-mercaptobenzonitrile (available from 4-cyanophenol by reaction with dimethylcarbamoyl chloride and thermal rearrangement), the following were prepared analogously:
difluoromethylthio-4 -(5 -methyl-1,3 -pyrimidin-2-yl) benzene
difluoromethylthio-4-(5-ethyl-1,3-pyrimidin-2-yl)-benzene
difluoromethylthio-4-(5-propyl-1,3-pyrimidin-2-yl) benzene
difluoromethylthio-4-(5-bury 1-1,3-pyrimidin-2-yl)-benzene
difluoromethylthio-4 -(5 -pentyl-1,3-pyrimidin-2-yl) benzene
difluoromethylthio-4-(5-hexyl-1,3-pyrimidin-2-yl)-benzene
difluoromethylthio-4-(5-heptyl-1,3-pyrimidin-2-yl) benzene
difluoromethylthio-4 -(5 -octyl -1,3 -pyrimidin-2-yl)-benzene
difluoromethylthio-4-(5-nonyl-1,3-pyrimidin-2-yl)-benzene difluoromethylthio-4-(5-decyl-1,3-pyrimidin-2-yl)-benzene
difluoromethylthio-4-(5-methoxy-1,3-pyrimidin-2-yl)-benzene
difluoromethylthio-4-(5-ethoxy-1,3-pyrimidin-2-yl)-benzene
difluoromethyl thio-4-(5-propoxy-1,3-pyrimidin-2-yl)-benzene
difluoromethylthio-4-(5-butoxy-1,3-pyrimidin-2-yl)benzene
difluoromethylthio-4-(5-pentoxy-1,3-pyrimidin-2-yl)benzene
difluoromethylthio-4-(5-hexoxy-1,3-pyrimidin-2-yl)benzene
difluoromethylthio-4-(5-heptoxy-1,3-pyrimidin-2-yl)benzene
difluoromethylthio-4-(5-octoxy-1,3-pyrimidin-2-yl)benzene
difluoromethylthio-4-(5-nonoxy-1,3-pyrimidin-2-yl)benzene
difluoromethylthio-4-(5-decoxy-1,3-pyrimidin-2-yl)benzene
difluoromethoxy-4-(5-methylpyridin-2-yl)-benzene
difluoromethoxy-4-(5-ethylpyridin-2-yl)-benzene
difluoromethoxy-4-(5-propylpyridin-2-yl)-benzene
difluoromethoxy-4-(5-butylpyridin-2-yl)-benzene
difluoromethoxy-4-(5-pentylpyridin-2-yl)-benzene
difluoromethoxy-4-(5-hexylpyridin-2-yl)-benzene
difluoromethoxy-4-(5-heptylpyridin-2-yl)-benzene
difluoromethoxy-4-(5-octylpyridin-2-yl)-benzene
difluoromethoxy-2-fluoro-4-(2-octylpyridin-5-yl)-benzene
difluoromethoxy-4-(5-nonylpyridin-2-yl)-benzene
difluoromethoxy-4-(5-decylpyridin-2-yl)-benzene
difluoromethoxy-4-(5-methoxypyridin-2-yl)-benzene
difluoromethoxy-4-(5-ethoxypyridin-2-yl)-benzene
difluoromethoxy-4-(5-propoxypyridin-2-yl)-benzene
difluoromethoxy-4-(5-butoxypyridin-2-yl)-benzene
difluoromethoxy-4-(5-pentoxypyridin-2-yl)-benzene
difluoromethoxy-4-(5-hexoxypyridin-2-yl)-benzene
difluoromethoxy-4-(5-heptoxypyridin-2-yl)-benzene
difluoromethoxy-4-(5-octoxypyridin-2-yl)-benzene
difluoromethoxy-2-fluoro-4-(2-octoxypyridin-5-yl)-benzene
difluoromethoxy-4-(5-nonoxypyridin-2-yl)-benzene
difluoromethoxy-4-(5-decoxypyridin-2-yl)-benzene
4-difluoromethoxy-4'-(5-methyl-1,3-pyrimidin-2-yl)biphenyl
4-difluoromethoxy-4'-(5-ethyl-1,3-pyrimidin-2-yl)-biphenyl
4-difluoromethoxy-4'-(5-propyl-1,3-pyrimidin-2-yl)-biphenyl
4-difluoromethoxy-4'-(5-butyl-1,3-pyrimidin-2-yl)-biphenyl
4-difluoromethoxy-4'-(5-pentyl-1,3-pyrimidin-2-yl)-biphenyl
4-difluoromethoxy-4'-(5-hexyl-1,3-pyrimidin-2-yl)-biphenyl
4-difluoromethoxy-4'-(5-heptyl-1,3-pyrimidin-2-yl)-biphenyl
4-difluoromethoxy-4'-(5-octyl-1,3-pyrimidin-2-yl)-biphenyl
4-difluoromethoxy-4'-(5-nonyl-1,3-pyrimidin-2-yl)-biphenyl
4-difluoromethoxy-4'-(5-decyl-1,3-pyrimidin-2-yl)-biphenyl

EXAMPLE 4

4-Benzyloxy-difluoromethoxy-benzene

A mixture of 40.0 g of hydroquinone monobenzyl ether, 40 g of NaOH, 200 ml of water and 300 ml of dioxane are heated to 70° C. with stirring. 35.5 g of chlorodifluoromethane are passed into the cooled mixture with vigorous stirring. The reaction mixture is poured into water, and the product is extracted with petroleum ether. The organic phase is dried over $Na_2SO_4$, evaporated, and the residue is chromatographed through a short silica gel column, using petroleum ether/ethyl acetate 8:2 as eluent. A colourless liquid is obtained.

EXAMPLE 4 a) Hydroquinone monodifluoromethyl ether

A solution of 25.0 g of the product from Example 4 in 100 ml of THF is hydrogenated at room temperature and atmospheric pressure, using 8 g of Pd/C (5% Pd) as catalyst. The catalyst is filtered off, and the filtrate is evaporated.

b) 4-Difluoromethoxyphenyl trans-4-pentylcyclohexanecarboxylate

A solution of 10.3 g of DCC in 50 ml of dichloromethane is added dropwise to a solution maintained at 0° C. of 9.92 g of trans-4-pentylcyclohexanecarboxylic acid, 8.11 g of hydroquinone monodifluoromethyl ether and 611 mg of 4-dimethylaminopyridine in 100 ml of dichloromethane. After stirring at room temperature for 18 hours, the precipitate formed is filtered off, and the filtrate is evaporated. The residue is chromatographed through a silica gel column, using petroleum ether/ethyl acetate 9:1 as eluent. Colourless crystals, m.p.: 54° C., c.p.: 30° C., $\Delta n=0.061$, viscosity: 16 are obtained.

The following are prepared analogously:
4-difluoromethoxyphenyl trans-4-ethylcyclohexanecarboxylate
4-difluoromethoxyphenyl trans-4-propylcyclohexanecarboxylate, m.p.: 54° C., c.p.: 0° C., $\Delta n=0.052$, viscosity: 10
4-difluoromethoxyphenyl trans-4-butylcyclohexanecarboxylate
4-difluoromethoxyphenyl trans-4-hexylcyclohexanecarboxylate
4-difluoromethoxyphenyl trans-4-heptylcyclohexanecarboxylate
4-difluoromethoxyphenyl trans-4-octylcyclohexanecarboxylate
4-difloromethoxyphenyl trans-4-nonylcyclohexanecarboxylate
4-difluoromethoxyphenyl trans-4-decylcyclohexanecarboxylate
4-difluoromethoxybiphenyl-4'-yl trans-4-methylcyclohexanecarboxylate
4-difluoromethoxybiphenyl-4'-yl trans-4-ethylcyclohexanecarboxylate
4-difluoromethoxybiphenyl-4'-yl trans-4-propylcyclohexanecarboxylate
4-difluoromethoxybiphenyl-4'-yl trans-4-butylcyclohexanecarboxylate
4-difluoromethoxybiphenyl-4'-yl trans-4-pentylcyclohexanecarboxylate
4-difluoromethoxybiphenyl-4'-yl trans-4-hexylcyclohexanecarboxylate 4-difluoromethoxybiphenyl -4'yl trans-4-heptylcyclohexanecarboxylate 4-difluoromethoxybiphenyl -4'-yl trans-4-octylcyclohexanecarboxylate 4-difluoromethoxybiphenyl-4'-yl trans -4-nonylcyclohexane carboxylate 4-difluoromethoxybiphenyl -4'-yl trans -4-decylcyclohexanecarboxylate 4-difluoromethoxyphenyl-4'-methyl trans,trans-bicyclo-hexane-4-carboxylate 4-difluoromethoxyphenyl-4'-ethyl trans,trans-bicyclo-hexane-4-carboxylate 4-difluoromethoxyphenyl-4'-propyl trans,trans-bicyclo-hexane-4-carboxylate 4-difluoromethoxyphenyl-4'-butyl trans,trans-bicyclo-hexane-4-carboxylate 4-difluoromethoxyphenyl-4'-pentyl trans,trans-bicyclo-hexane-4-carboxylate, m.p.: 61° C., c.p.: 196.9° C., $\Delta n = 0.089$ 4-difluoromethoxyphenyl-4'-hexyl trans,trans-bicyclo-hexane-4-carboxylate 4-difluoromethoxyphenyl-4'-heptyl trans,trans-bicyclo-hexane-4-carboxylate 4-difluoromethoxyphenyl-4'-octyl trans,trans-bicyclo-hexane-4-carboxylate 4-difluoromethoxyphenyl-4'-nonyl trans,trans-bicyclo-hexane-4-carboxylate 4-difluoromethoxyphenyl-4'-decyl trans, trans-bicyclo-hexane-4-carboxylate Using 4-difluoromethylthiophenol (obtainable by esterification of 4-hydroxybenzenesulfonic acid (Aldrich) with acetic acid, conversion to the sulfonyl chloride, reduction to the thiol using zinc/hydrochloric acid, etherification analogously to Example 1) and alkaline ether cleavage), the following were prepared analogously:

4-difluoromethylthiophenyl trans-4-methylcyclohexanecarboxylate 4-difluoromethylthiophenyl trans-4-ethylcyclohexanecarboxylate 4-difluoromethylthiophenyl trans-4-propylcyclohexanecarboxylate 4-difluoromethylthiophenyl trans-4-butylcyclohexanecarboxylate 4-difluoromethylthiophenyl trans-4-pentylcyclohexanecarboxylate 4-difluoromethylthiophenyl trans-4-hexylcyclohexanecarboxylate 4-difluoromethylthiophenyl trans-4-heptylcyclohexanecarboxylate 4-difluoromethylthiophenyl trans-4-octylcyclohexanecarboxylate 4-difluoromethylthiophenyl trans-4-nonylcyclohexanecarboxylate 4-difluoromethylthiophenyl trans-4-decylcyclohexanecarboxylate 3-fluoro-4-difluoromethylthiophenyl-4'-methyl trans, trans-bicyclohexane-4-carboxylate 3-fluoro-4-difluoromethylthiophenyl-4'-ethyl trans, trans-bicyclohexane-4-carboxylate 3-fluoro-4-difluoromethylthiophenyl-4'-propyl trans, trans-bicyclohexane-4-carboxylate 3-fluoro-4-difluoromethylthiophenyl-4'-butyl trans, trans-bicyclohexane-4-carboxylate 3-fluoro-4-difluoromethylthiophenyl-4'-pentyl trans, trans-bicyclohexane-4-carboxylate 3-fluoro-4-difluoromethylthiophenyl-4'-hexyl trans, trans-bicyclohexane-4-carboxylate 3-fluoro-4-difluoromethylthiophenyl-4'-heptyl trans, trans-bicyclohexane-4-carboxylate 3-fluoro-4-difluoromethylthiophenyl-4'-octyl trans, trans-bicyclohexane-4-carboxylate 3-fluoro-4-difluoromethylthiophenyl-4'-nonyl trans, trans-bicyclohexane-4-carboxylate 3-fluoro-4-difluoromethylthiophenyl-4'-decyl trans, trans-bicyclohexane-4-carboxylate 2,3-difluoro-4-difluoromethylthiophenyl trans-4-methylcyclohexanebenzoate 2,3-difluoro-4-difluoromethylthiophenyl trans-4-ethylcyclohexanebenzoate 2,3-difluoro-4-difluoromethylthiophenyl trans-4-propylcyclohexanebenzoate 2,3-difluoro-4-difluoromethylthiophenyl trans-4-butylcyclohexanebenzoate 2,3-difluoro-4-difluoromethylthiophenyl trans-4-pentylcyclohexanebenzoate 2,3-difluoro-4-difluoromethylthiophenyl trans-4-hexylcyclohexanebenzoate 2,3-difluoro-4-difluoromethylthiophenyl trans-4-heptylcyclohexanebenzoate 2,3-difluoro-4-difluoromethylthiophenyl trans-4-octylcyclohexanebenzoate 2,3-difluoro-4-difluoromethylthiophenyl trans-4-nonylcyclohexanebenzoate 2,3-difluoro-4-difluoromethylthiophenyl trans-4-decylcyclohexanebenzoate

EXAMPLE 6 a)

4-[2-(4-Benzyloxyphenyl)ethenyl]-4'-pentyl-trans,trans-bicyclohexyl 49.6 g of 4-benzyloxybenzaldehyde and 25.9 g of KOT are added to a suspension of 147.1 g of 4'-pentyl trans,trans-bicyclohexyl-4-methyltriphenylphosphonium iodide in 1 l of THF with ice-cooling. The mixture is stirred for 1 h at 5° C. 2 N HCl is then added, until the aqueous phase is neutral, and water is added until the precipitate has been dissolved. The organic phase is separated off, dried over Na$_2$SO$_4$ and evaporated. The residue is chromatographed through a silica gel column, using petroleum ether/ethyl acetate 95:5 as eluent. Colorless crystals are obtained.

b)

4-[2-(4-Hydroxyphenyl)ethyl]-4'-pentyl-trans,trans-bicyclohexyl

A solution of 34.6 g of product 6a in 200 ml of THF is hydrogenated at room temperature and atmospheric pressure, using 10 g of Pd/C (5% Pd) as catalyst. The catalyst is filtered off, and the filtrate is evaporated. A grey crystalline solid is obtained;

c)

4-[2-(4-Difluoromethoxyphenyl)ethyl]-4'-pentyl-trans,-trans-bicyclohexyl

The product 6b is converted to the difluoromethoxy compound analogously to Example 1, m.p.: 24° C., c.p.: 149.9° C., $\Delta n = 0.097$, viscosity: 21. d) The phosphonium iodide from 6 a) is reacted directly with 4-difluoromethoxybenzaldehyde, as described in 6 a), and hydrogenated analogously to 6 b).

The following are prepared analogously:

4-[2-(4-difluoromethoxyphenyl)ethyl]-4'-ethyl-trans, trans-bicyclohexyl

4-[2-(4-difluoromethoxyphenyl)ethyl]-4'-propyl-trans, trans-bicyclohexyl
4-[2-(4-difluoromethoxyphenyl)ethyl]-4'-butyl-trans, trans-bicyclohexyl
4-[2-(4-difluoromethoxyphenyl)ethyl]-4'-hexyl-trans, trans-bicyclohexyl
4-[2-(4-difluoromethoxyphenyl)ethyl]-4'-heptyl-trans, trans-bicyclohexyl
4-[2-(4-difluoromethoxyphenyl)ethyl]-4'-octyl-trans, trans-bicyclohexyl
4-[2-(4-difluoromethoxyphenyl)ethyl]-4'-nonyl-trans, trans-bicyclohexyl
4-[2-(4-difluoromethoxyphenyl)ethyl]-4'-decyl-trans, trans-bicyclohexyl
4-[2-(2,3-difluoro-4-difluoromethoxyphenyl)ethyl]-4'-methyl-trans, trans-bicyclohexyl
4-[2-(2,3-difluoro-4-difluoromethoxyphenyl) ethyl]-4'-ethyl-trans, trans-bicyclohexyl
4-[2-(2,3-difluoro-4-difluoromethoxyphenyl)ethyl]-4'-propyl-trans, trans-bicyclohexyl, 81 N 128 I
4-[2-(2,3-difluoro-4-difluoromethoxyphenyl)ethyl]-4'-butyl-trans,trans-bicyclohexyl
4-[2-(2,3-difluoro-4-difluoromethoxyphenyl)ethyl]-4'-pentyl-trans,trans-bicyclohexyl
4-[2-(2,3-difluoro-4-difluoromethoxyphenyl)ethyl]-4,-hexyl-trans,trans-bicyclohexyl
4-[2-(2,3-difluoro-4-difluoromethoxyphenyl)ethyl]-4'-heptyl-trans,trans-bicyclohexyl
4-[2-(2,3-difluoro-4-difluoromethoxyphenyl)ethyl]-4'-octyl-trans,trans-bicyclohexyl
4-[2-(2,3-difluoro-4-difluoromethoxyphenyl)ethyl]-4'-nonyl-trans,trans-bicyclohexyl
4-[2-(2,3-difluoro-4-difluoromethoxyphenyl)ethyl]-4'-decyl-trans,trans-bicyclohexyl
4-[2-(trans-4-methylcyclohexyl)ethyl]-4'-difluoromethoxybiphenyl
4-[2-(trans-4-ethylcyclohexyl)ethyl]-4'-difluoromethoxybiphenyl
4-[2-(trans-4-propylcyclohexyl)ethyl]-4'-difluoromethoxybiphenyl
4-[2-(trans-4-butylcyclohexyl)ethyl]-4'-difluoromethoxybiphenyl
4-[2-(trans-4-pentylcyclohexyl)ethyl]-4'-difluoromethoxybiphenyl
4-[2-(trans-4-hexylcyclohexyl)ethyl]-4'-difluoromethoxybiphenyl
4-[2-(trans-4-heptylcyclohexyl)ethyl]-4'-difluoromethoxybiphenyl
4-[2-(trans-4-octylcyclohexyl)ethyl]-4'-difluoromethoxybiphenyl
4-[2-(trans-4-nonylcyclohexyl)ethyl]-4'-difluoromethoxybiphenyl
4-[2-(trans-4-decylcyclohexyl)ethyl]-4'-difluoromethoxybiphenyl
4-difluoromethoxy-[2-(trans-4-methylcyclohexyl)ethyl]benzene
4-difluoromethoxy-[2-(trans-4-ethylcyclohexyl)ethyl]benzene,
m.p.: −37° C., c.p. (extrapolated): −60° C., Δn=0.033, viscosity: 6
4-difluoromethoxy-[2-(trans-4-propylcyclohexyl)ethyl]benzene,
m.p.: −2° C., c.p.: −14.5° C., Δn=0.042, viscosity: 6
4-difluoromethoxy-[2-(trans-4-butylcyclohexyl)ethyl]benzene
4-difluoromethoxy-[2-(trans-4-pentylcyclohexyl)ethyl]benzene,
m.p.: 4° C., c.p.: 5.1° C., Δn: 0.065, viscosity: 7
4-difluoromethoxy-[2-(trans-4-hexylcyclohexyl)ethyl]benzene
4-difluoromethoxy-[2-(trans-4-heptylcyclohexyl)ethyl]benzene,
m.p.: 30° C., c.p.: 16.9° C., Δn=0.065, viscosity:
4-difluoromethoxy-[2-(trans-4-octylcyclohexyl)ethyl]benzene
4-difluoromethoxy-[2-(trans-4-nonylcyclohexyl)ethyl]benzene
4-difluoromethoxy-[2-(trans-4-decylcyclohexyl)ethyl]benzene

EXAMPLE 7 a) 4-(1H,1H-Difluoroethoxy)-benzaldehyde 16.4 g of 2,2-difluoroethanol are added to a suspension of 3.3 g of sodium hydride in 100 ml of 1,3-dimethyl-2-imidazolidinone, and the mixture is stirred at 30° C. for 2 hours. It is cooled to 0°–10° C., and 12.4 g of 4-fluorobenzaldehyde are added. The mixture is stirred at 5° C. for 2 hours and at 90° C. for 4 hours. After cooling, the reaction mixture is poured into 200 ml of 5% HCl, and the product is extracted with ether. The organic phase is dried over $Na_2SO_4$, evaporated, and the residue is distilled. A colourless liquid is obtained.

b) 4-{2-[4-(1H,1H-Difluoroethoxy)-phenyl]-ethenyl}-4'-pentyl-trans,trans-bicyclohexyl 17.1 g of the product 7a and 9.3 g of KOT are added to a suspension of 53 g of 4'-pentyl-trans,trans-bicyclohexyl-4-methyltriphenylphosphonium iodide in 250 ml of THF with ice-cooling. The mixture is stirred at 5° C. for 1 hour. 2 N HCl is then added until the aqueous phase is neutral, and water is added until the precipitate has been dissolved. The organic phase is separated off, dried over $Na_2SO_4$ and evaporated. The residue is chromatographed through a silica gel column, using petroleum ether/ethyl acetate 9:1 as eluent. Colourless crystals are obtained.

The following are prepared analogously:
4-{2-[4-(1H,1H-difluoroethoxy)-phenyl]-ethenyl}-4'-ethyl-trans,trans-bicyclohexyl
4-{2-[4-(1H,1H-difluoroethoxy)-phenyl]-ethenyl}-4'-propyl-trans,trans-bicyclohexyl
4-{2-[4-(1H,1H-difluoroethoxy)-phenyl]-ethenyl}-4'-butyl-trans,trans-bicyclohexyl
4-{2-[4-(1H,1H-difluoroethoxy)-phenyl]-ethenyl}-4'-hexyl-trans,trans-bicyclohexyl
4-{2-[4-(1H,1H-difluoroethoxy)-phenyl]-ethenyl}-4'-heptyl-trans,trans-bicyclohexyl
4-{2-[4-(1H,1H-difluoroethoxy)-phenyl]-ethenyl}-4'-octyl-trans,trans-bicyclohexyl
4-{2-[4-(1H, 1H-difluoroethoxy)-phenyl]-ethenyl }-4'-nonyl-trans,trans-bicyclohexyl
4-{2-[4-(1H, 1H-difluoroethoxy)-phenyl]-ethenyl }-4'-decyl-trans,trans-bicyclohexyl
4-difluoromethoxy-[2-(trans-4-methoxycyclohexyl)-ethenyl]-benzene
4-difluoromethoxy-[2-(trans-4-ethoxycyclohexyl)-ethenyl]-benzene
4-difluoromethoxy-[2-(trans-4-propoxycyclohexyl)-ethenyl]-benzene
4-difluoromethoxy-[2-(trans-4-butoxycyclohexyl)-ethenyl]-benzene
4-difluoromethoxy-[2-(trans-4-pentoxycyclohexyl)-ethenyl]-benzene 4-difluoromethoxy-[2-(trans-4-hexoxycyclohexyl)-ethenyl]-benzene
4-difluoromethoxy-[2-(trans-4-heptoxycyclohexyl)-ethenyl]-benzene
4-difluoromethoxy-[2-(trans-4-octoxycyclohexyl)-ethenyl]-benzene
4-difluoromethoxy-[2-(trans-4-nonoxycyclohexyl)-ethenyl]-benzene
4-difluoromethoxy-[2-(trans-4-decoxycyclohexyl)-ethenyl]-benzene

EXAMPLE 8

4-{2-[4-1H,1H-Difluoroethoxy)-phenyl]-ethyl}-4′-pentyl-trans,trans-bicyclohexyl 10 g of Pd/C (5% Pd) are added to a solution of 16.8 g of product 7b in 150 ml of ethyl acetate, and the mixture is hydrogenated at room temperature and atmospheric pressure. The catalyst is filtered off, the filtrate is evaporated, and the residue is recrystallized from ethanol. Colourless crystals are obtained.

The following are prepared analogously:
4-{2-[4-1H,1H-difluoroethoxy)-phenyl]-ethyl}-4′-ethyl-trans,trans-bicyclohexyl
4-{2-[4-1H,1H-difluoroethoxy)-phenyl]-ethyl}-4′-propyl-trans,trans-bicyclohexyl
4-{2-[4-1H,1H-difluoroethoxy)-phenyl]-ethyl}-4′-butyl-trans,trans-bicyclohexyl
4-{2-[4-1H,1H-difluoroethoxy)-phenyl]-ethyl}-4′-hexyl-trans,trans-bicyclohexyl
4-{2-[4-1H,1H-difluoroethoxy)-phenyl]-ethyl}-4′-heptyl-trans,trans-bicyclohexyl
4-{2-[4-1H-difluoroethoxy)-phenyl]-ethyl}-4′-octyl-trans,trans-bicyclohexyl
4-{2-[4-1H,1H-difluoroethoxy)-phenyl]-ethyl}-4′-nonyl-trans,trans-bicyclohexyl
4-{2-[4-1H,1H-difluoroethoxy)-phenyl]-ethyl}-4′-decyl-trans,trans-bicyclohexyl

EXAMPLE 9 a) 3-[4-(trans-4-Propylcyclohexyl)-phenyl]-propanoic acid

A solution of 12.6 g of 3-[4-(trans-4-propyl-cyclohexyl)-phenyl]-propenoic acid (obtained by condensation of 4-(trans-propylcyclohexyl)-benzaldehyde with malonic acid in pyridine) in 120 ml of ethyl acetate is hydrogenated at room temperature and atmospheric pressure, using 4 g of Pd/C (5% Pd) as catalyst. The catalyst is filtered off, and the filtrate is evaporated. Colourless crystals are obtained.

b) 3-[4-(trans-4-Propylcyclohexyl)-phenyl]-propanol

A solution of 11.3 g of product 9a in 50 ml of THF is added dropwise to a suspension maintained at 0° C. of 1.52 g of lithium alanate in 200 ml of THF. After stirring at room temperature for 2 hours, the reaction mixture is poured into water and acidified with 13% HCl. The mixture is extracted with ether, the organic phase is dried and evaporated. Colourless crystals are obtained.

c) 3-[4-(trans-4-Propylcyclohexyl)-phenyl]-propanol

A solution of 7.2 g of dimethyl sulfoxide in 12 ml of dichloromethane is added dropwise to a solution maintained at −75° C. of 5.7 g of oxalyl chloride in 80 ml of dichloromethane, and the mixture is stirred for 5 minutes. A solution of 10.3 g of product 9b in 20 ml of dichloromethane is then added dropwise, and the mixture is stirred for another 15 minutes. 28 ml of triethylamine are then added, the mixture is allowed to reach 0° C., and 100 ml of water and 200 ml of ether are added. The organic phase is separated off, washed with water and saturated NaCl solution, dried over $Na_2SO_4$ and evaporated. The residue is chromatographed through a silica gel column using petroleum ether/ethyl acetate 8:2 as eluent. A colourless oil is obtained.

d) 1-(3,3-Difluoropropyl)-4-(trans-4-propylcyclohexyl)-benzene

A solution of 4.1 g of DAST in 50 ml of hexane is added dropwise to a solution of 7.9 g of product 9c in 100 ml of hexane, and the mixture is stirred at room temperature for 2 hours. 100 ml of water are added, and the organic phase is separated off, dried over $Na_2SO_4$ and evaporated. The residue is chromatographed through a silica gel column, using petroleum ether as eluent, and is distilled in a kugelrohr apparatus. A colourless liquid is obtained. m.p.: 12° C., c.p.: −60° C. (extrapolated), Δn=0.032, viscosity: 11.

The following are prepared analogously:
1-(3,3-difluoropropyl)-4-(trans-4-ethylcyclohexyl)-benzene
1-(3,3-difluoropropyl)-4-(trans-4-butylcyclohexyl)-benzene
1-(3,3-difluoropropyl)-4-(trans-4-pentylcyclohexyl)-benzene
1-(3,3-difluoropropyl)-4-(trans-4-hexylcyclohexyl)-benzene
1-(3,3-difluoropropyl)-4-(trans-4-heptylcyclohexyl)-benzene
1-(3,3-difluoropropyl)-4-(trans-4-octylcyclohexyl)-benzene
1-(3,3-difluoropropyl)-4-(trans-4-nonylcyclohexyl)-benzene
1-(3,3-difluoropropyl)-4-(trans-4-decylcyclohexyl)-benzene

EXAMPLE 10

1H,1H-Difluoroethyl 4′-pentyl-trans,trans-bicyclohexane-4-carboxylate

A mixture of 36.5 g of 4′-pentyl-trans,trans-bicyclohexane-4-carboxylic acid and 50 ml of thionyl chloride is heated to boiling for 1 hour. Excess thionyl chloride is distilled off, 50 ml of toluene are added to the residue, and the mixture is transferred to a dropping funnel. This solution is added dropwise to a solution of 11.9 g of 2,2-difluoroethanol and 43.3 ml of pyridine in 100 ml of toluene. The reaction mixture is heated to boiling for 1 hour and then left to stand at room temperature for 18 hours. 100 ml of 2 N HCl are added, and the organic phase is separated off. The organic phase is washed twice with water, dried over $Na_2SO_4$ and evaporated. The residue is taken up in 50 ml of THF and 50 ml of 5% aqueous ammonia, and the mixture is stirred for 1 hour. It is extracted with petroleum ether, the organic phase is dried over $Na_2SO_4$ and evaporated. The residue is recrystallized from acetonitrile. Colourless crystals are obtained.

The following are prepared analogously:
1H,1H-difluoroethyl 4′-ethyl-trans,trans-bicyclohexane-4-carboxylate
1H,1H-difluoroethyl 4′-propyl-trans,trans-bicyclohexane-4-carboxylate
1H,1H-difluoroethyl 4′-butyl-trans,trans-bicyclohexane-4-carboxylate 1H,1H-difluoroethyl 4'-hexyl-trans,trans-bicyclohexane-4-carboxylate
1H,1H-difluoroethyl 4'-heptyl-trans,trans-bicyclohexane-4-carboxylate
1H,1H-difluoroethyl 4'-octyl-trans,trans-bicyclohexane-4-carboxylate
1H,1H-difluoroethyl 4'-nonyl-trans,trans-bicyclohexane-4-carboxylate
1H,1H-difluoroethyl 4'-decyl-trans,trans-bicyclohexane-4-carboxylate
1H,1H-difluoroethyl trans-4-(4-methylphenyl)-cyclohexanecarboxylate
1H,1H-difluoroethyl trans-4-(4-ethylphenyl)-cyclohexanecarboxylate
1H,1H-difluoroethyl trans-4-(4-propylphenyl)-cyclohexanecarboxylate
1H,1H-difluoroethyl trans-4-(4-butylphenyl)-cyclohexanecarbonlate
1H,1H-difluoroethyl trans-4-(4-pentylphenyl)-cyclohexanecarboxylate
1H,1H-difluoroethyl trans-4-(4-hexylphenyl)-cyclohexanecarboxylate
1H,1H-difluoroethyl trans-4-(4-heptylphenyl)-cyclohexanecarboxylate
1H,1H-difluoroethyl trans-4-(4-octylphenyl)-cyclohexanecarboxylate
1H,1H-difluoroethyl trans-4-(4-nonylphenyl)-cyclohexanecarboxylate
1H,1H-difluoroethyl trans-4-(4-decylphenyl)-cyclohexanecarboxylate
1H,1H-difluoroethyl trans-4-(4-methoxyphenyl)-cyclohexanecarboxylate
1H,1H-difluoroethyl trans-4-(4-ethoxyphenyl)-cyclohexanecarboxylate
1H,1H-difluoroethyl trans-4-(4-propoxyphenyl)-cyclohexanecarboxylate
1H,1H-difluoroethyl trans-4-(4-butoxyphenyl)-cyclohexanecarboxylate
1H,1H-difluoroethyl trans-4-(4-pentoxyphenyl)-cyclohexanecarboxylate
1H,1H-difluoroethyl trans-4-(3-fluoro-4-pentoxyphenyl)cyclohexanecarboxylate
1H,1H-difluoroethyl trans-4-(4-hexoxyphenyl)-cyclohexanecarboxylate
1H,1H-difluoroethyl trans-4-(4-heptoxyphenyl)-cyclohexanecarboxylate
1H,1H-difluoroethyl trans-4-(4-octoxyphenyl)-cyclohexanecarboxylate
1H,1H-difluoroethyl trans-4-(4-nonoxyphenyl)-cyclohexanecarboxylate
1H,1H-difluoroethyl trans-4-(4-decoxyphenyl)-cyclohexanecarboxylate
1H, 1H-difluoroethyl 4-(trans-4-ethylcyclohexyl)-benzoate
1H, 1H-difluoroethyl 4-(trans-4-propylcyclohexyl)-benzoate
1H, 1H-difluoroethyl 4-(trans-4-butylcyclohexyl)-benzoate
1H, 1H-difluoroethyl 4-(trans-4-pentylcyclohexyl)-benzoate
1H, 1H-difluoroethyl 4-(trans-4-hexylcyclohexyl)-benzoate
1H, 1H-difluoroethyl 4-(trans-4-heptylcyclohexyl)-benzoate
1H, 1H-difluoroethyl 4-(trans-4-octylcyclohexyl)-benzoate
1H, 1H-difluoroethyl 4-(trans-4-nonylcyclohexyl)-benzoate
1H, 1H-difluoroethyl 4-(trans-4-decylcyclohexyl)-benzoate

EXAMPLE 11 a) 4-(trans-4-Formylcyclohexyl)-4'-pentylbiphenyl 112 ml of a 20% solution of DIBALH in hexane are added dropwise to a solution of 33.2 g of 4-(trans-4-cyanocyclohexyl)-4'-pentylbiphenyl in 1 l of pentane, and the mixture is stirred for 18 hours. Water is then added dropwise until the evolution of gas subsides and then 200 ml of 25% sulfuric acid are added dropwise. The organic phase is separated off, dried over $Na_2SO_4$ and evaporated. Colourless deliquescent crystals are obtained.

b) 4-(trans-4-Difluoromethylcyclohexyl)-4'-pentyl-biphenyl

A solution of 6.9 g of DAST in 10 ml of dichloromethane is added dropwise to a solution of 18.0 g of product 11a in 30 ml of dichloromethane at room temperature, and the mixture is stirred for 18 hours. 150 ml of water are added, the organic phase is separated off, dried over $Na_2SO_4$ and evaporated. The residue is chromatographed through a silica gel column, using petroleum ether/ethyl acetate 95:5. Colourless crystals are obtained.

The following are prepared analogously:
4-(trans-4-difluoromethylcyclohexyl)-4'-ethylbiphenyl
4-(trans-4-difluoromethylcyclohexyl)-2',3'-difluoro-4'-propylbiphenyl
4-(trans-4-difluoromethylcyclohexyl)-4'-propylbiphenyl
4-(trans-4-difluoromethylcyclohexyl)-4'-butylbiphenyl
4-(trans-4-difluoromethylcyclohexyl)-4'-hexylbiphenyl
4-(trans-4-difluoromethylcyclohexyl)-4'-heptylbiphenyl
4-(trans-4-difluoromethylcyclohexyl)-4'-octylbiphenyl
4-(trans-4-difluoromethylcyclohexyl)-4'-nonylbiphenyl
4-(trans-4-difluoromethylcyclohexyl)-4'-decylbiphenyl
4-(trans-4-difluoromethylcyclohexyl)-4'-methoxybiphenyl
4-(trans-4-difluoromethylcyclohexyl)-4'-ethoxybiphenyl
4-(trans-4-difluoromethylcyclohexyl)-3'-cyano-4'-ethoxybiphenyl
4-(trans-4-difluoromethylcyclohexyl)-4'-propoxybiphenyl
4-(trans-4-difluoromethylcyclohexyl)-4'-butoxybiphenyl
4-(trans-4-difluoromethylcyclohexyl)-4'-pentoxybiphenyl
4-(trans-4-difluoromethylcyclohexyl)-4'-hexoxybiphenyl
4-(trans-4-difluoromethylcyclohexyl)-4'-heptoxybiphenyl
4-(trans-4-difluoromethylcyclohexyl)-4'-octoxybiphenyl
4-(trans-4-difluoromethylcyclohexyl)-4'-nonoxybiphenyl 4-(trans-4-difluoromethylcyclohexyl)-4'-decoxybiphenyl

EXAMPLE 12 a)

4'-Propyl-trans,trans-bicyclohexane-4-carboxaldehyde

A solution of 59.6 g of 4-hydroxymethyl-4'-propyl-trans,trans-bicyclohexyl in 200 ml of dichloromethane is added dropwise to a suspension of 82.0 g of PCC in 400 ml of dichloromethane. After stirring for 2 hours, 200 ml of ether are added. The mixture is filtered, and the residue is washed with ether. The filtrate is evaporated, and the residue is chromatographed through a short silica gel column, using toluene as eluent. A colourless oil is obtained.

b) 4-Difluoromethyl-4'-propyl-trans,trans-bicyclohexyl

A solution of 2.7 ml of DAST in 30 ml of hexane is added dropwise to a solution of 4.9 g of product 12a in 100 ml of hexane at room temperature, and the mixture is stirred for 18 hours. 100 ml of water are added, the organic phase is separated off, dried over Na$_2$SO$_4$ and evaporated. The residue is chromatographed through a silica gel column, using petroleum ether as eluent: a colourless liquid is obtained. m.p.: 19° C., c.p.: 17° C., Δn=0.003, viscosity: 10.

The following are prepared analogously:
4-difluoromethyl-4'-ethyl-trans,trans-bicyclohexyl
4-difluoromethyl-4'-butyl-trans,trans-bicyclohexyl
4-difluoromethyl-4'-pentyl-trans,trans-bicyclohexyl m.p.: 29° C., c.p.: 32.1° C., Δn=0.0, viscosity: 14
4-difluoromethyl-4'-hexyl-trans,trans-bicyclohexyl
4-difluoromethyl-4'-heptyl-trans,trans-bicyclohexyl
4-difluoromethyl-4'-octyl-trans,trans-bicyclohexyl
4-difluoromethyl-4'-nonyl-trans,trans-bicyclohexyl
4-difluoromethyl-4'-decyl-trans,trans-bicyclohexyl

EXAMPLE 13 a) 1-Difluoromethoxy-4-iodobenzene 100 g (0.455 mol) of 4-iodophenol and 54.6 g (1.365 mol) of sodium hydroxide are added to a mixture of 300 ml of THF and 30 ml of water. After stirring for about ½ hour, the mixture is evaporated in a rotary evaporator; this is repeated after the addition of 200 ml of toluene. The residue is taken up in 400 ml of THF. The mixture is cooled to 0° C., 47.1 g (0.545 mol) of chlorodifluoromethane are introduced, and the mixture is then stirred for 1 hour. It is then stirred at about +5° C. for 18 hours. The solution above the resulting slurry-like precipitate was decanted off. It was evaporated in a rotary evaporator, and the residue was chromatographed through a silica gel column, using petroleum ether as eluent.

The following were prepared analogously:
1-difluoromethoxy-4-bromobenzene
1-difluoromethoxy-2-fluoro-4-bromobenzene b)

4-Difluoromethoxy-4'-(trans-4-pentylcyclohexyl)-tolan

A solution of 15.3 g of 4-(trans-4-pentylcyclohexyl)-phenylacetylene (available from the acetophenone by dehydration, using PCl$_5$/KOT), 16.2 g of difluoromethoxy-4-iodobenzene, 100 ml of triethylamine, 0.085 g of bis(triphenylphosphine)dichloropalladium and 0.11 g of copper(I) iodide is stirred at room temperature for 3 hours. The cloudy mixture is stirred into dilute hydrochloric acid (500 ml of water +200 ml of 37% hydrochloric acid), extracted with t-butyl methyl ether and worked up as usual. m.p.: 62° C., c.p.: 203.1° C.

The following were prepared analogously:
4-difluoromethoxy-4'-(trans-4-methylcyclohexyl)-tolan
4-difluoromethoxy-4'-(trans-4-ethylcyclohexyl)-tolan
4-difluoromethoxy-4'-(trans-4-propylcyclohexyl)-tolan, m.p.: 87° C., c.p.: 212° C.
4-difluoromethoxy-4'-(trans-4-butylcyclohexyl)-tolan
4-difluoromethoxy-4'-(trans-4-pentylcyclohexyl)-tolan
4-difluoromethoxy-4'-(trans-4-hexylcyclohexyl)-tolan
4-difluoromethoxy-4'-(trans-4-heptylcyclohexyl)-tolan
4-difluoromethoxy-4'-(trans-4-octylcyclohexyl)-tolan
4-difluoromethoxy-4'-(trans-4-nonylcyclohexyl)-tolan
4-difluoromethoxy-4'-(trans-4-decylcyclohexyl)-tolan
4-difluoromethoxy-4'-[2-(trans-4-methylcyclohexyl)ethyl]-tolan
4-difluoromethoxy-4'-[2-(trans-4-ethylcyclohexyl)ethyl]tolan
4-difluoromethoxy-4'-[2-(trans-4-propylcyclohexyl)ethyl]tolan
4-difluoromethoxy-4'-[2-(trans-4-butylcyclohexyl)ethyl]tolan
4-difluoromethoxy-4'-[2-(trans-4-pentylcyclohexyl)ethyl]tolan
4-difluoromethoxy-4'-[2-(trans-4-hexylcyclohexyl)ethyl]tolan
4-difluoromethoxy-4'-[2-(trans-4-heptylcyclohexyl)ethyl]tolan
4-difluoromethoxy-4'-[2-(trans-4-octylcyclohexyl)ethyl]tolan
4-difluoromethoxy-4'-[2-(trans-4-nonylcyclohexyl)ethyl]tolan
4-difluoromethoxy-4'-[2-(trans-4-decylcyclohexyl)ethyl]tolan
4-difluoromethoxy-4'-methyl-tolan
4-difluoromethoxy-4'-ethyl-tolan
4-difluoromethoxy-4'-propyl-tolan m.p.: 50° C., c.p. (extrapolated): 10° C., viscosity: 7
4-difluoromethoxy-4'-butyl-tolan
4-difluoromethoxy-4'-pentyl-tolan
4-difluoromethoxy-4'-hexyl-tolan
4-difluoromethoxy-4'-heptyl-tolan
4-difluoromethoxy-4'-octyl-tolan
4-difluoromethoxy-4'-nonyl-tolan
4-difluoromethoxy-4'-decyl-tolan Using 4-(difluoromethylthio)-iodobenzene (obtainable by chlorosulfonation of iodobenzene, reduction to the 4-mercaptoiodobenzene, using zinc in dilute hydrochloric acid, and etherification analogously to Example 1), the following were prepared analogously:
4-difluoromethylthio-4'-(trans-4-methylcyclohexyl)-tolan
4-difluoromethylthio-4'-(trans-4-ethylcyclohexyl)-tolan
4-difluoromethylthio-4'-(trans-4-propylcyclohexyl)-tolan
4-difluoromethylthio-4'-(trans-4-butylcyclohexyl)-tolan
4-difluoromethylthio-4'-(trans-4-pentylcyclohexyl)-tolan
4-difluoromethylthio-4'-(trans-4-hexylcyclohexyl)-tolan 4-difluoromethylthio-4'-(trans-4-heptylcyclohexyl)-tolan
4-difluoromethylthio-4'-(trans-4-octylcyclohexyl)-tolan
4-difluoromethylthio-4'-(trans-4-nonylcyclohexyl)-tolan
4-difluoromethylthio-4'-(trans-4-decylcyclohexyl)-tolan

EXAMPLE 14

4-(2,2-Difluoroethyl)-4'-pentyl-trans,trans-bicyclohexyl 13 g of 4-(2-oxoethyl)-4'-pentyl-trans,transbicyclohexyl (available from bicyclohexanecarboxylic acid, reduction to the alcohol, conversion to the nitrile and conversion to the aldehyde with DIBALH) are dissolved in 100 ml of hexane. At room temperature, a solution of 6.2 ml of DAST in 100 ml of hexane is added dropwise, and stirring of the mixture at room temperature is continued for 10 hours. It is then worked up as usual. m.p.: −1° C., c.p.: 82° C., Δn=0.040, viscosity: 11

The following were prepared analogously:
4-(2,2-difluoroethyl)-4'-methyl-trans,trans-bicyclohexyl
4-(2,2-difluoroethyl)-4'-ethyl-trans,trans-bicyclohexyl
4-(2,2-difluoroethyl)-4'-propyl-trans,trans-bicyclohexyl
4-(2,2-difluoroethyl)-4'-butyl-trans,trans-bicyclohexyl
4-(2,2-difluoroethyl)-4'-hexyl-trans,trans-bicyclohexyl
4-(2,2-difluoroethyl)-4'-heptyl-trans,trans-bicyclohexyl
4-(2,2-difluoroethyl)-4'-octyl-trans,trans-bicyclohexyl
4-(2,2-difluoroethyl)-4'-nonyl-trans,trans-bicyclohexyl
4-(2,2-difluoroethyl)-4'-decyl-trans,trans-bicyclohexyl

EXAMPLE 15

1-(4-Ethoxyphenyl)-2-(4'-difluoromethoxyphenyl)-ethene 22.2 g of 4-ethoxystyrene, 33.5 g of 4-(difluoromethoxy)bromobenzene (available from 4-bromophenol analogously to Example 1)), 0.67 g of palladium(II) acetate, 20.8 ml of triethylamine and 1.83 g of tri-o-tolylphosphine are heated to boiling in 225 ml of acetonitrile for 24 hours. After cooling to 0° C., the crystals are filtered off with suction and washed with acetonitrile and water. m.p.: 177° C.

The following were prepared analogously:
1-(4-methoxyphenyl)-2-(4'-difluoromethoxyphenyl)-ethene
1-(4-propoxyphenyl)-2-(4'-difluoromethoxyphenyl)-ethene
1-(4-butoxyphenyl)-2-(4'-difluoromethoxyphenyl)-ethene
1-(4-pentoxyphenyl)-2-(4'-difluoromethoxyphenyl)-ethene
1-(4-hexoxyphenyl)-2-(4'-difluoromethoxyphenyl)-ethene
1-(4-heptoxyphenyl)-2-(4'-difluoromethoxyphenyl)-ethene
1-(4-octoxyphenyl)-2-(4'-difluoromethoxyphenyl)-ethene
1-(4-nonoxyphenyl)-2-(4'-difluoromethoxyphenyl)-ethene
1-(4-decoxyphenyl)-2-(4'-difluoromethoxyphenyl)-ethene
1-[4-(trans-4-methylcyclohexyl)-phenyl]-2-(4'-difluoromethoxyphenyl)-ethene
1-[4-(trans-4-ethylcyclohexyl)-phenyl]-2-(4'-difluoromethoxyphenyl)-ethene
1-[4-(trans-4-propylcyclohexyl)-phenyl]-2-(4'-difluoromethoxyphenyl)-ethene
1-[4-(trans-4-butylcyclohexyl)-phenyl]-2-(4'-difluoromethoxyphenyl)-ethene
1-[4-(trans-4-pentylcyclohexyl)-phenyl]-2-(4'-difluoromethoxyphenyl)-ethene
1-[4-(trans-4-hexylcyclohexyl)-phenyl]-2-(4'-difluoromethoxyphenyl)-ethene
1-[4-(trans-4-heptylcyclohexyl)-phenyl]-2-(4'-difluoromethoxyphenyl)-ethene
1-[4-(trans-4-octylcyclohexyl)-phenyl]-2-(4'-difluoromethoxyphenyl)-ethene
1-[4-(trans-4-nonylcyclohexyl)-phenyl]-2-(4'-difluoromethoxyphenyl)-ethene
1-[4-(trans-4-decylcyclohexyl)-phenyl]-2-(4'-difluoromethoxyphenyl)-ethene
1-[4-(5-methyl-1,3-pyrimidin-2-yl)-phenyl]-2-(4'-difluoromethoxyphenyl)-ethene
1-[4-(5-ethyl-1,3-pyrimidin-2-yl)-phenyl]-2-(4'-difluoromethoxyphenyl)-ethene
1-[4-(5-propyl-1,3-pyrimidin-2-yl)-phenyl]-2-(4'-difluoromethoxyphenyl)-ethene
1-[4-(5-butyl-1,3-pyrimidin-2-yl)-phenyl]-2-(4'-difluoromethoxyphenyl)-ethene
1-[4-(5-pentyl-1,3-pyrimidin-2-yl)-phenyl]-2-(4'-difluoromethoxyphenyl)-ethene
1-[4-(5-hexyl-1,3-pyrimidin-2-yl)-phenyl]-2-(4'-difluoromethoxyphenyl)-ethene
1-[4-(5-heptyl-1,3-pyrimidin-2-yl)-phenyl]-2-(4'-difluoromethoxyphenyl)-ethene
1-[4-(5-octyl-1,3-pyrimidin-2-yl)-phenyl]-2-(4'-difluoromethoxyphenyl)-ethene
1-[4-(5-nonyl-1,3-pyrimidin-2-yl)-phenyl]-2-(4'-difluoromethoxyphenyl)-ethene
1-[4-(5-decyl-1,3-pyrimidin-2-yl)-phenyl]-2-(4'-difluoromethoxyphenyl)-ethene

EXAMPLE 16

1-(4-Ethoxyphenyl)-2-(4'-difluoromethoxyphenyl)-ethane 19.7 g of 1-(4-ethoxyphenyl)-2-(4'-difluoromethoxyphenyl)-ethene are hydrogenated in 150 ml of THF analogously to Example 6b, using 6 g of Pd/C (5% Pd) as catalyst. m.p.: 37° C., Δn=0.103, viscosity: 8

The following were prepared analogously:
1-(4-methoxyphenyl)-2-(4'-difluoromethoxyphenyl)-ethane
1-(4-propoxyphenyl)-2-(4'-difluoromethoxyphenyl)-ethane
1-(4-butoxyphenyl)-2-(4'-difluoromethoxyphenyl)-ethane
1-(4-pentoxyphenyl)-2-(4'-difluoromethoxyphenyl)-ethane
1-(4-hexoxyphenyl)-2-(4'-difluoromethoxyphenyl)-ethane
1-(4-heptoxyphenyl)-2-(4'-difluoromethoxyphenyl)-ethane
1-(4-octoxyphenyl)-2-(4'-difluoromethoxyphenyl)-ethane 1-(4-nonoxyphenyl)-2-(4'-difluoromethoxyphenyl)-ethane
1-(4-decoxyphenyl)-2-(4'-difluoromethoxyphenyl)-ethane
1-(4-methylphenyl)-2-(4-difluoromethoxybiphenyl-4'-yl)ethane
1-(4-ethylphenyl)-2-(4-difluoromethoxybiphenyl-4'-yl)ethane
1-(4-propylphenyl)-2-(4-difluoromethoxybiphenyl-4'-yl)ethane
1-(4-butylphenyl)-2-(4-difluoromethoxybiphenyl-4'-yl)ethane
1-(4-pentylphenyl)-2-(4-difluoromethoxybiphenyl-4,-yl)-ethane
1-(4-hexylphenyl)-2-(4-difluoromethoxybiphenyl-4'-yl)ethane
1-(4-heptylphenyl)-2-(4-difluoromethoxybiphenyl-4'-yl)ethane
1-(4-octylphenyl)-2-(4-difluoromethoxybiphenyl-4'-yl)ethane
1-(4-nonylphenyl)-2-(4-difluoromethoxybiphenyl-4'-yl)ethane
1-(4-decylphenyl)-2-(4-difluoromethoxybiphenyl-4'-yl)ethane
1-(4-methoxyphenyl)-2-(4-difluoromethoxybiphenyl-4'-yl)ethane
1-(4-ethoxyphenyl)-2-(4-difluoromethoxybiphenyl-4'-yl)ethane, m.p: 153°, c.p. (extrapolated): 110°, Δn: 0.118
1-(4-propoxyphenyl)-2-(4-difluoromethoxybiphenyl-4'-yl)ethane
1-(4-butoxyphenyl)-2-(4-difluoromethoxybiphenyl-4'-yl)ethane
1-(4-pentoxyphenyl)-2-(4-difluoromethoxybiphenyl-4'-yl)ethane
1-(4-hexoxyphenyl)-2-(4-difluoromethoxybiphenyl-4'-yl)ethane
1-(4-heptoxyphenyl)-2-(4-difluoromethoxybiphenyl-4'-yl)ethane
1-(4-octoxyphenyl)-2-(4-difluoromethoxybiphenyl-4'-yl)ethane
1-(4-nonoxyphenyl)-2-(4-difluoromethoxybiphenyl-4'-yl)ethane
1-(4-decoxyphenyl)-2-(4-difluoromethoxybiphenyl-4'-yl)ethane
1-[4-(trans-4-methylcyclohexyl)-phenyl]-2-(4'-difluoromethoxyphenyl)-ethane
1-[4-(trans-4-ethylcyclohexyl)-phenyl]-2-(4'-difluoromethoxyphenyl)-ethane
1-[4-(trans-4-propylcyclohexyl)-phenyl]-2-(4'-difluoromethoxyphenyl)-ethane, m.p.: 51° c, c.p.: 79.6° C., Δn= 0.125
1-[4-(trans-4-butylcyclohexyl)-phenyl]-2-(4,-difluoromethoxyphenyl)-ethane
1-[4-(trans-4-pentylcyclohexyl)-phenyl]-2-(4'-difluoromethoxyphenyl)-ethane, m.p.: 32° C., c.p.: 90.2° C., Δn=0.123
1-[4-(trans-4-hexylcyclohexyl)-phenyl]-2-(4'-difluoromethoxyphenyl)-ethane
1-[4-(trans-4-heptylcyclohexyl)-phenyl]-2-(4'-difluoromethoxyphenyl)-ethane
1-[4-(trans-4-octylcyclohexyl)-phenyl]-2-(4'-difluoromethoxyphenyl)-ethane
1-[4-(trans-4-nonylcyclohexyl)-phenyl]-2-(4'-difluoromethoxyphenyl)-ethane
1-[4-(trans-4-decylcyclohexyl)-phenyl]-2-(4'-difluoromethoxyphenyl)-ethane
1-[4-(trans-4-methylcyclohexyl)-phenyl]-2-(4'-difluoromethylthiophenyl)-ethane
1-[4-(trans-4-ethylcyclohexyl)-phenyl]-2-(4'-difluoromethylthiophenyl)-ethane
1-[4-(trans-4-propylcyclohexyl)-phenyl]-2-(4'-difluoromethylthiophenyl)-ethane
1-[4-(trans-4-butylcyclohexyl)-phenyl]-2-(4'-difluoromethylthiophenyl)-ethane
1-[4-(trans-4-pentylcyclohexyl)-phenyl]-2-(4'-difluoromethylthiophenyl)-ethane
1-[4-(trans-4-hexylcyclohexyl)-phenyl]-2-(4'-difluoromethylthiophenyl)-ethane
1-[4-(trans-4-heptylcyclohexyl)-phenyl]-2-(4'-difluoromethylthiophenyl)-ethane
1-[4-(trans-4-octylcyclohexyl)-phenyl]-2-(4'-difluoromethylthiophenyl)-ethane
1-[4-(trans-4-nonylcyclohexyl)-phenyl]-2-(4'-difluoromethylthiophenyl)-ethane
1-[4-(trans-4-decylcyclohexyl)-phenyl]-2-(4'-difluoromethylthiophenyl)-ethane
1-[4-(5-methyl-1,3-pyrimidin-2-yl)-phenyl]-2-(4'-difluoromethoxyphenyl)-ethane
1-[4-(5-ethyl-1,3-pyrimidin-2-yl)-phenyl]-2-(4'-difluoromethoxyphenyl)-ethane
1-[4-(5-propyl-1,3-pyrimidin-2-yl)-phenyl]-2-(4'-difluoromethoxyphenyl)-ethane
1-[4-(5-butyl-1,3-pyrimidin-2-yl)-phenyl]-2-(4'-difluoromethoxyphenyl)-ethane
1-[4-(5-pentyl-1,3-pyrimidin-2-yl)-phenyl]-2-(4'-difluoromethoxyphenyl)-ethane
1-[4-(5-hexyl-1,3-pyrimidin-2-yl)-phenyl]-2-(4'-difluoromethoxyphenyl)-ethane
1-[4-(5-heptyl-1,3-pyrimidin-2-yl)-phenyl]-2-(4'-difluoromethoxyphenyl)-ethane
1-[4-(5-octyl-1,3-pyrimidin-2-yl)-phenyl]-2-(4'-difluoromethoxyphenyl)-ethane
1-[4-(5-nonyl-1,3-pyrimidin-2-yl)-phenyl]-2-(4'-difluoromethoxyphenyl)-ethane
1-[4-(5-decyl-1,3-pyrimidin-2-yl)-phenyl]-2-(4'-difluoromethoxyphenyl)-ethane

EXAMPLE 17

4-(trans-4-Propylcyclohexyl)-phenyl 4-difluoromethoxybenzoate

4-Difluoromethoxybenzoic acid (available by etherification of the phenolic OH group of p-hydroxybenzyl alcohol analogously to Example 1, followed by oxidation with potassium permanganate) is esterified, as described in Example 5b), with 4-(trans-4-propylcyclohexyl)-phenol by the DCC method. m.p.: 104° C., c.p.: 193.5° C.

The following were prepared analogously:

4-(trans-4-methylcyclohexyl)-phenyl 4-difluoromethoxybenzoate
4-(trans-4-ethylcyclohexyl)-phenyl 4-difluoromethoxybenzoate
4-(trans-4-butylcyclohexyl)-phenyl 4-difluoromethoxybenzoate
4-(trans-4-pentylcyclohexyl)-phenyl 4-difluoromethoxybenzoate
4-(trans-4-hexylcyclohexyl)-phenyl 4-difluoromethoxybenzoate
4-(trans-4-heptylcyclohexyl)-phenyl 4-difluoromethoxybenzoate
4-(trans-4-nonylcyclohexyl)-phenyl 4-difluoromethoxybenzoate 4-(trans-4-octylcyclohexyl)-phenyl 4-difluoromethoxybenzoate
4-(trans-4-decylcyclohexyl)-phenyl 4-difluoromethoxybenzoate
4-methylphenyl 4-difluoromethoxybenzoate
4-ethylphenyl 4-difluoromethoxybenzoate (sic)
4-propylphenyl 4-difluoromethoxybenzoate
4-butylphenyl 4-difluoromethoxybenzoate
4-pentylphenyl 4-difluoromethoxybenzoate
4-hexylphenyl 4-difluoromethoxybenzoate
4-heptylphenyl 4-difluoromethoxybenzoate
4-octylphenyl 4-difluoromethoxybenzoate
4-nonylphenyl 4-difluoromethoxybenzoate
4-decylphenyl 4-difluoromethoxybenzoate
4-methylbiphenyl-4-yl 4-difluoromethoxybenzoate
4'-ethylbiphenyl-4-yl 4-difluoromethoxybenzoate
4'-propylbiphenyl-4-yl 4-difluoromethoxybenzoate
4'-butylbiphenyl-4-yl 4-difluoromethoxybenzoate
4'-pentylbiphenyl-4-yl 4-difluoromethoxybenzoate
4'-hexylbiphenyl-4-yl 4-difluoromethoxybenzoate
4'-heptylbiphenyl-4-yl 4-difluoromethoxybenzoate
4'-octylbiphenyl-4-yl 4-difluoromethoxybenzoate
4'-nonylbiphenyl-4-yl 4-difluoromethoxybenzoate
4'-decylbiphenyl-4-yl 4-difluoromethoxybenzoate Using 4-difluoromethylthiobenzoic acid (available from p-toluenesulfonic acid by oxidation to give the carboxylic acid, esterification, conversion to the sulfonyl chloride, reduction, using zinc/hydrochloric acid, etherification analogously to Example 1 and liberation of the acid), the following are obtained analogously:

4-(trans-4-methylcyclohexyl)-phenyl 4-difluoromethylthiobenzoate
4-(trans-4-ethylcyclohexyl)-phenyl 4-difluoromethylthiobenzoate
4-(trans-4-propylcyclohexyl)-phenyl 4-difluoromethylthiobenzoate
4-(trans-4-butylcyclohexyl)-phenyl 4-difluoromethylthiobenzoate
4-(trans-4-pentylcyclohexyl)-phenyl 4-difluoromethylthiobenzoate
4-(trans-4-hexylcyclohexyl)-phenyl 4 -difluoromethylthiobenzoate
4-(trans-4-heptylcyclohexyl)-phenyl 4-difluoromethylthiobenzoate
4-(trans-4-octylcyclohexyl)-phenyl 4-difluoromethylthiobenzoate
4-(trans-4-nonylcyclohexyl)-phenyl 4-difluoromethylthiobenzoate
4-(trans-4-decylcyclohexyl)-phenyl 4-difluoromethylthiobenzoate The following examples refer to liquid-crystalline phases according to the invention.

Example A

A liquid-crystalline phase consisting of:
10% of p-trans-4-propylcyclohexylbenzonitrile
10% of p-trans-4-butylcyclohexylbenzonitrile
10% of p-trans-4-pentylcyclohexylbenzonitrile (sic)
20% of difluoromethoxy-4-(trans-4-pentylcyclohexyl)-benzene
10% of trans-1-p-ethoxyphenyl-4-propylcyclohexane
8% of trans-1-p-butoxyphenyl-4-propylcyclohexane
5% of 4'-p-propylphenyl trans-4-(trans-4-propylcyclohexyl)-cyclohexanecarboxylate
5% of 4'-p-pentylphenyl trans-4-(trans-4-propylcyclohexyl)-cyclohexanecarboxylate
5% of 4'-p-propylphenyl trans-4-(trans-4-butylcyclohexyl)-cyclohexanecarboxylate
5% of 4'-p-pentylphenyl trans-4-(trans-4-butylcyclohexyl)-cyclohexanecarboxylate
4% of 4-(trans-4-propylcyclohexyl)-2'-fluoro-4'-(trans-4-propylcyclohexyl)-biphenyl
4% of 2-fluoro-4-(trans-4-pentylcyclohexyl)-4'-(trans-4-propylcyclohexyl)biphenyl and
4% of 4-(trans-4-pentylcyclohexyl)-2'-fluoro-4'-(trans-4-pentylcyclohexyl)-biphenyl has a melting point of $-18.8°$ C., a clear point of 78° C. and a viscosity of 16 mm$^2$/s at 20° C.

Example B

A liquid-crystalline phase consisting of
15% of difluoromethoxy-4-(trans-4-propylcyclohexyl)benzene
17% of difluoromethoxy-4-(trans-4-pentylcyclohexyl)benzene
13% of difluoromethoxy-4-(trans-4-heptylcyclohexyl)benzene
10% of trans-1-p-methoxyphenyl-4-propylcyclohexane
10% of trans-1-p-ethoxyphenyl-4-propylcyclohexane
5% of trans-1-p-butoxyphenyl-4-propylcyclohexane
5% of 4-(trans-4-propylcyclohexyl)-2'-fluoro-4'-(trans-4-propylcyclohexyl)-biphenyl
5% of 2-fluoro-4-(trans-4-pentylycyclohexyl)-4'-(trans-4-propylcyclohexyl)-biphenyl (sic)
5% of 4-(trans-4-pentylcyclohexyl)-2'-fluoro-4'-(trans-4-pentylcyclohexyl)-biphenyl
5% of 4,4'-bis-(trans-4-propylcyclohexyl)-biphenyl
5% of 4-(trans-4-pentylcyclohexyl)-4'-(trans-4-propylcyclohexyl)-biphenyl and
5% of 4,4'-bis-(trans-4-pentylcyclohexyl)-biphenyl has a melting point of $-20.8°$ C., a clear point of 72° C. and a viscosity of 12 mm$^2$/s at 20° C.

Example C

A liquid-crystalline phase consisting of
16% of p-trans-4-propylcyclohexyl-benzonitrile
4% of p-trans-4-pentylcyclohexyl-benzonitrile
18% of 1-(3,3-difluoropropyl)-4-(trans-4-propylcyclohexyl)-benzene
10% of trans-1-p-methoxyphenyl-4-propylcyclohexane
10% of trans-1-p-ethoxyphenyl-4-propylcyclohexane
11% of 4-ethyl-4'-(trans-4-propylcyclohexyl)-biphenyl
11% of 4-ethyl-4'-(trans-4-pentylcyclohexyl)-biphenyl
3% of 4-(trans-4-propycyclohexyl)-2'-fluoro-4'-(trans-4-propylcyclohexyl)-biphenyl (sic)
4% of 2-fluoro-4-(trans-4-pentylcyclohexyl)-4'-(trans-4-propylcyclohexyl)-biphenyl
3% of 4-(trans-4-pentylcyclohexyl)-2'-fluoro-4'-(trans-4-pentylcyclohexyl)-biphenyl
3% of 4,4'-bis-(trans-4-propylcyclohexyl)-biphenyl
4% of 4-(trans-4-pentylcyclohexyl)-4'-(trans-4-propylcyclohexyl)-biphenyl and
3% of 4,4'-bis-(trans-4-pentylcyclohexyl)-biphenyl has a melting point of $-10.3°$ C., a clear point of 91° C. and a viscosity of 17 mm$^2$/s at 20° C.

Example D

A liquid-crystalline phase consisting of
24% of p-trans-4-propylcycloyhexyl-benzonitrile
36% of p-trans-4-pentylcyclohexyl-benzonitrile
25% of p-trans-4-heptylcyclohexyl-benzonitrile 15% of 4-cyano-4'-(trans-4-pentylcyclohexyl)-biphenyl has a clear point of 71° C., a Δn of 0.140 and a viscosity of 28.

This phase is mixed with 10% of one of the following compounds I according to the invention. The values of this phase according to the invention obtained are summarized in Table 1 below.

Compounds I 1  4-difluoromethoxy-4'-octoxy-biphenyl
2  difluoromethoxy-4-(trans-4-propylcyclohexyl)-benzene
3  difluoromethoxy-4-(trans-4-pentylcyclohexyl)-benzene
4  4-[2-(4-difluoromethoxyphenyl)-ethyl]-4'-pentyl-trans,trans-bicyclohexyl
5  difluoromethoxy-4-(5-heptyl-1,3-pyrimidin-2-yl)-benzene
6  4-difluoromethoxy-4'-(trans-4-pentylcyclohexyl)-biphenyl

TABLE 1

| I | c.p. [°C.] | Δn | Viscosity |
|---|---|---|---|
| 1 | 65.4 | 0.1349 | 26.8 |
| 2 | 60.2 | 0.1291 | 23.8 |
| 3 | 61.8 | 0.1313 | 24.5 |
| 4 | 76.7 | 0.1353 | 27.4 |
| 5 | 63.7 | 0.1368 | 26.7 |
| 6 | 76.1 | 0.1411 | 28.2 |

Example E

A liquid-crystalline phase consisting of

22% of trans-1-p-ethylphenyl-4-propylcyclohexane
20% of trans -1 -p-methoxyphenyl -4 -propylcyclohexane
15% of trans-1-p-ethoxyphenyl-4-propylcyclohexane
19% of 4-ethyl-4'-(trans-4-propylcyclohexyl)-biphenyl
14% of 4-ethyl-4'-(trans-4-pentylcyclohexyl)-biphenyl
5% of 4-(trans-4-propylcyclohexyl)-4'-(trans-4-propylcyclohexyl)-biphenyl
5% of 4-(trans-4-pentylcyclohexyl)-4'-(trans-4-propylcyclohexyl)-biphenyl has a clear point of 72° C., a Δn of 0.1131 and a viscosity of 11.

This phase is mixed with 10% of one of the following compounds I according to the invention. The values of this phase according to the invention obtained are summarized in Table 2 below.

Compounds I 7  4 -difluoromethoxyphenyl trans -4 -pentyl -cyclohexanecarboxylate
8  4-difluoromethoxyphenyl 4'-pentyl-trans, trans-bicyclohexane-4-carboxylate

TABLE 2

| I | c.p. [°C.] | Δn | Viscosity |
|---|---|---|---|
| 7 | 67.8 | 0.1080 | 11,9 |
| 8 | 82.7 | 0.1108 | 12.6 |

We claim:

1. A liquid-crystalline medium containing at least two liquid-crystalline components, and based on a mixture of polar compounds having positive dielectric anisotropy, wherein at least one compound is of the formula I R—(A$^1$—Z$^1$)$_m$—A$^2$—Q—CHF$_2$    I in which
R is H, halogen, —CN, —NCS, an alkyl or alkenyl radical having 1 to 15 carbon atoms, in which one or more CH$_2$ groups in these radicals, independently of one another, can each also be replaced by —O—, —S—,

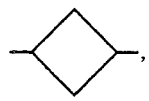

—CO—, —CO—O—, —O—CO— or —O—CO—O— in such a manner that oxygen atoms are not directly linked to one another, or such an alkyl or alkenyl radical substituted by CN, CF$_3$ or at least one halogen atom.

A$^1$ and A$^2$ independently of one another are each a
(a) trans-1,4-cyclohexylene radical in which one or more non-adjacent CH$_2$ groups can also be replaced by —O— and/or —S—,
(b) 1,4-phenylene radical in which one or two CH groups can also be replaced by N,
(c) radical from the group consisting of 1,4-cyclohexenylene, 1,4-bicyclo[2,2,2]octylene, piperidine-1,4-diyl, naphthalene-2,6-diyl, decahydronaphthalene,2,6-diyl and 1,2,3,4-tetrahydronaphthalene-2,6-diyl, in which the radicals (a) and (b) can be substituted by CN or fluorine, Z$^1$ is —CO—O, —CH$_2$O—, —CH$_2$CH$_2$, —CH=CH—, —C≡C— or a single bond,
m is 1, 2 or 3 and
Q is —O—, —S—, —CH$_2$, —CO—O—, —O—CO—, or a single bond.

2. A liquid crystal display element, containing a liquid-crystalline medium according to claim 1.

3. Electrooptical display element, containing a liquid-crystalline medium according to claim 1 as a dielectric.

4. A medium according to claim 1 wherein R is alkyl or alkoxy.

5. A medium according to claim 1, wherein R is a perfluoroalkyl radical in which fluorine is optionally partially replaced by hydrogen.

6. A medium according to claim 1, wherein A$^1$ and/or A$^2$ are 1,4-phenylene which is monosubstituted or disubstituted by F.

7. A medium according to claim 1, wherein A$^1$ and A$^2$ are each independently F-substituted 1,4-phenylene radicals of the formulae

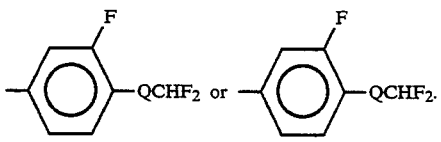

8. A medium according to claim 3, wherein the compound of the formula I is Icd or Ifh,

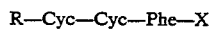    Icd

R—Cyc—Cyc—CH₂CH₂—Phe—X   Ifh in which
Cyc is a 1,4-cyclohexylene radical,
Phe is a 1,4-phenylene radical, and
X is QCHF₂.

9. A medium according to claim 1, wherein the compound of the formula I is
4-[2-(4-difluoromethoxyphenyl)ethyl]-4'-propyl-trans,trans-bicyclohexyl,
4-[2-(4-difluoromethoxyphenyl)ethyl]-4'-ethyl-trans,-transbicyclohexyl,
4-[2-(4-difluoromethoxyphenyl)ethyl]-4'-butyl-trans,-transbicyclohexyl,
4-[2-(4-difluoromethoxyphenyl)ethyl]-4'-hexyl-trans,transbicyclohexyl,
4-[2-(4-difluoromethoxyphenyl)ethyl]-4'-heptyl-trans,trans-bicyclohexyl,
4-[2-(4-difluoromethoxyphenyl)ethyl]-4'-octyl-trans,-transbicyclohexyl,
4-[2-(4-difluoromethoxyphenyl)ethyl]-4'-nonyl-trans,transbicyclohexyl,
4-[2-(4-difluoromethoxyphenyl)ethyl]-4'-decyl-trans,transbicyclohexyl,
4-[2-(2,3-difluoro-4-difluoromethoxyphenyl)ethyl]-4'-methyl-trans,trans-bicyclohexyl,
4-[2-(2,3-difluoro-4-difluoromethoxyphenyl)ethyl]-4'-ethyl-trans,trans-bicyclohexyl,
4-[2-(2,3-difluoro-4-difluoromethoxyphenyl)ethyl]-4'-propyl-trans,trans-bicyclohexyl,
4-[2-(2,3-difluoro-4-difluoromethoxyphenyl)ethyl]-4'-butyl-trans,trans-bicyclohexyl,
4-[2-(2,3-difluoro-4-difluoromethoxyphenyl)ethyl]-4'-pentyl-trans,trans-bicyclohexyl,
4-[2-(2,3-difluoro-4-difluoromethoxyphenyl)ethyl]-4'-hexyl-trans,trans-bicyclohexyl,
4-[2-(2,3-difluoro-4-difluoromethoxyphenyl)ethyl]-4'-heptyl-trans,trans-bicyclohexyl,
4-[2-(2,3-difluoro-4-difluoromethoxyphenyl)ethyl]-4'-octyl-trans,trans-bicyclohexyl,
4-[2-(2,3-difluoro-4-difluoromethoxyphenyl)ethyl]-4'-nonyl-trans,trans-bicyclohexyl, or
4-[2-(2,3-difluoro-4-difluoromethoxyphenyl)ethyl]-4'-decyl-trans,trans-bicyclohexyl.

10. A medium according to claim 1, wherein the compound of the formula I is
4-methyl-4'-(4-difluoromethoxyphenyl)-trans,trans-bicyclohexyl,
4-trifluoromethyl-4'-(4-difluoromethoxyphenyl)-trans,trans-bicyclohexyl,
4-ethyl-4'-(4-difluoromethoxyphenyl)-trans,trans-bicyclohexyl,
4-propyl-4'-(4-difluoromethoxyphenyl)-trans,trans-bicyclohexyl,
4-isopropyl-4'-(4-difluoromethoxyphenyl)-trans,-transbicyclohexyl,
4-butyl-4'-(4-difluoromethoxyphenyl)-trans,trans-bicyclohexyl,
4-methoxyethyl-4'-(4-difluoromethoxyphenyl)-trans,-transbicyclohexyl,
4-pentyl-4'-(4-difluoromethoxyphenyl)-trans,trans-bicyclohexyl,
4-hexyl-4'-(4-difluoromethoxyphenyl)-trans,trans-bicyclohexyl,
4-heptyl-4'-(4-difluoromethoxyphenyl)-trans,trans-bicyclohexyl,
4-octyl-4'-(4-difluoromethoxyphenyl)-trans,trans-bicyclohexyl,
4-nonyl-4'-(4-difluoromethoxyphenyl)-trans,trans-bicyclohexyl, or
4-decyl-4'-(4-difluoromethoxyphenyl)-trans,trans-bicyclohexyl.

11. A medium according to claim 1, wherein $Z^1$ is a single bond, —CO—O—, —CH₂CH₂—, —CH₂O— or —OCH₂—.

12. A medium according to claim 1, wherein m is 1 or 2.

13. A medium according to claim 1, wherein Q is a single bond, —O—, —S—, or —COO—.

14. A medium according to claim 1, wherein the proportion of compounds of formula I is 1 to 40%.

15. A medium according to claim 1 containing more than 40% of compounds of the formula I.

16. A medium according to claim 1, wherein Q is a single bond or —O—.

* * * * *

UNITED STATES PATENT AND TRADEMARK OFFICE
CERTIFICATE OF CORRECTION

PATENT NO. : 5,389,292
DATED : February 14, 1995
INVENTOR(S) : Dieter DORSCH et al.

It is certified that error appears in the above-indentified patent and that said Letters Patent is hereby corrected as shown below:

Claim 1; column 42, line 38: Delete "$CH_2$,"

Claim 1; column 42, line 38: Delete "—O—;"

Claim 1; column 42, line 39: Change "CO—," to -- —O—CO— --.

Claim 7; column 42, line 60: In the formulae insert -- F -- as shown: 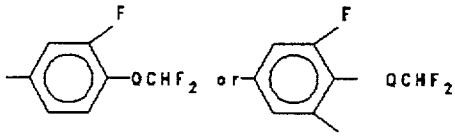 or 

Signed and Sealed this

Eleventh Day of July, 1995

Attest:

BRUCE LEHMAN

*Attesting Officer*   *Commissioner of Patents and Trademarks*